(12) United States Patent
Mallone et al.

(10) Patent No.: US 11,078,251 B2
(45) Date of Patent: Aug. 3, 2021

(54) T CELL RECEPTORS (TCR) AND USES THEREOF FOR THE DIAGNOSIS AND TREATMENT OF DIABETES

(71) Applicants: INSERM (INSTITUT NATIONAL DE LA SANTÉ ET DE LA RECHERCHE MÉDICALE), Paris (FR); UNIVERSITÉ PARIS DESCARTES, Paris (FR); CENTRE NATIONAL DE LA RECHERCHE SCIENTIFIQUE (CNRS), Paris (FR)

(72) Inventors: Roberto Mallone, Paris (FR); Georgia Afonso, Paris (FR); Ana Ines Lalanne, Paris (FR); Slobodan Culina, Paris (FR)

(73) Assignees: INSERM (Institut National de la Santé et de la Recherche Médicale), Paris (FR); Université Paris Descartes, Paris (FR); Centre National de la Recherche Scientifique (CNRS), Paris (FR)

( * ) Notice: Subject to any disclaimer, the term of this patent is extended or adjusted under 35 U.S.C. 154(b) by 464 days.

(21) Appl. No.: 15/756,091

(22) PCT Filed: Sep. 16, 2016

(86) PCT No.: PCT/EP2016/071980
§ 371 (c)(1),
(2) Date: Feb. 28, 2018

(87) PCT Pub. No.: WO2017/046335
PCT Pub. Date: Mar. 23, 2017

(65) Prior Publication Data
US 2018/0244746 A1 Aug. 30, 2018

(30) Foreign Application Priority Data

Sep. 18, 2015 (EP) ..................................... 15306456

(51) Int. Cl.
*C07K 14/725* (2006.01)
*G01N 33/566* (2006.01)
*C12Q 1/6881* (2018.01)
*C12N 15/86* (2006.01)

(52) U.S. Cl.
CPC .......... *C07K 14/7051* (2013.01); *C12N 15/86* (2013.01); *C12Q 1/6881* (2013.01); *G01N 33/566* (2013.01); *C07K 2319/00* (2013.01); *C07K 2319/33* (2013.01); *G01N 2333/7051* (2013.01)

(58) Field of Classification Search
CPC ............ C07K 14/7051; C07K 2319/00; C07K 2319/33; C12N 15/86; C12Q 1/6881; G01N 33/566; G01N 2333/7051
See application file for complete search history.

(56) References Cited

PUBLICATIONS

Rudikoff et al., PNAS 79: 1979-1983 (Year: 1983).*
Jubala et al., Vet Pathol 42: 468-476 (Year: 2005).*
Roitt et al., in Immunology second edition, Gower Medical Publishing New York, p. 5.8 and 5.9 (Year: 1989).*
Database EMBL [Online], Dec. 4, 1995, "*Homo sapiens* (human) partial T-cell receptor alpha", XP002763499, retrieved from EBI accession No. EMBL: AAA82669 Database accession No. AAA82669 abstract & Barber D F et al: :T cell receptor diversity in alloreactive responses against HLA-B27 (B*2705) is limited by multiple-level restrictions iin both alpha and beta chains., European Journal of Immunology Sep. 1995, vol. 25, No. 9, Sep. 1995, pp. 2479-2485.
Database EMBL [Online], Apr. 1, 2010, "*Mus musculus* (house mouse) partial T-cell receptor beta chain", XP002763500, retrieved from EBI accession No. EMBL:ADD98776, Database accession No. ADD98776 abstract & B. G. Vincent et al: "Toxin-Coupled MHC Class I Tetramers Can Specifically Ablate Autoreactive CD8+ T Cells and Delay Diabetes in Nonobese Diabetic Mice", The Journal of Immunology, vol. 184, No. 8, Mar. 10, 2010, pp. 4196-4204, XP055314112.
Database Geneseq [Online], Jul. 16, 2015, "Human TCR alpha chain TRAV26/TRAJ26 CDR3, Seq ID 1986,", retrieved from EBI accession No. GSP: BCA45443 Database accession No. BCA45443 abstract & WO 2015/075939 A1 (Repertoire Genesis Inc [JP]) May 29, 2015.
Database Geneseq [Online], Jun. 4, 2015, "Human TCR beta CDR3, Seq ID 161." XP002763502, retrieved from EBI accession No. GSP:BBY16298, Database accession No. BBY16298 abtstract & US 2015/104441 A1 (Olweus Johanna [NO] et al) Apr. 16, 2015.
Database EMBL [Online], Jul. 1, 1992, "*Homo sapiens* (human) partial T-cell receptor alpha", XP002763503, retrieved from EBI accession No. AAA61068 abstract & Lauzurica P et al: "Asymmetric selection of T-cell antigen receptor alpha- and beta-chains in HLA-B27 alloreactivity", The Journal of Immunology. vol. 148, No. 11, Jun. 1, 1992, pp. 3624-3630.
Database EMBL [Online], Jul. 30, 2015, "*Homo sapiens* (human) partial T Cell receptor alpha chain V-J-region", CP002763504, retrieved from EBI accession No. EMBL: BAS03244.
Brendan K. Reed et al: "Detection of Constant Domain of Human T Cell Antigen Receptor Alpha-Chain via Novel Monoclonal Antibody 7F18", Monoclonal Antibodies in Immunodiagnosis and Immunotherapy, vol. 33, No. 6, Dec. 1, 2014, pp. 386-392.

(Continued)

*Primary Examiner* — Phuong Huynh
(74) *Attorney, Agent, or Firm* — W&C IP

(57) ABSTRACT

The present invention relates to T-cell receptors (TCR) that recognize pancreatic betacell epitopes and uses thereof for the diagnosis and treatment of diabetes.

1 Claim, 28 Drawing Sheets

Specification includes a Sequence Listing.

(56) References Cited

PUBLICATIONS

Zhijun Liu et al: "Prevention of Type 1 Diabetes in the Rat With an Allele-Specific Anti-T-Cell Receptor Antibody", Diabetes, vol. 61, No. 5, May 19, 2012, pp. 1160-1797.

Scotto M et al: "Zinc transporter (ZnT) 8 is an immunodominant CD8+ T cell epitope in HLA-A2 type 1 diabetic patients", Diabetalogia, vol. 55, No. 7, Apr. 20, 2012, pp. 2026-2031, XP035067376, Clinical and Experimental Diabetes and Metabolism, Springer, Berlin, DE ISSN: 1432-0428.

* cited by examiner

Figure 2A:
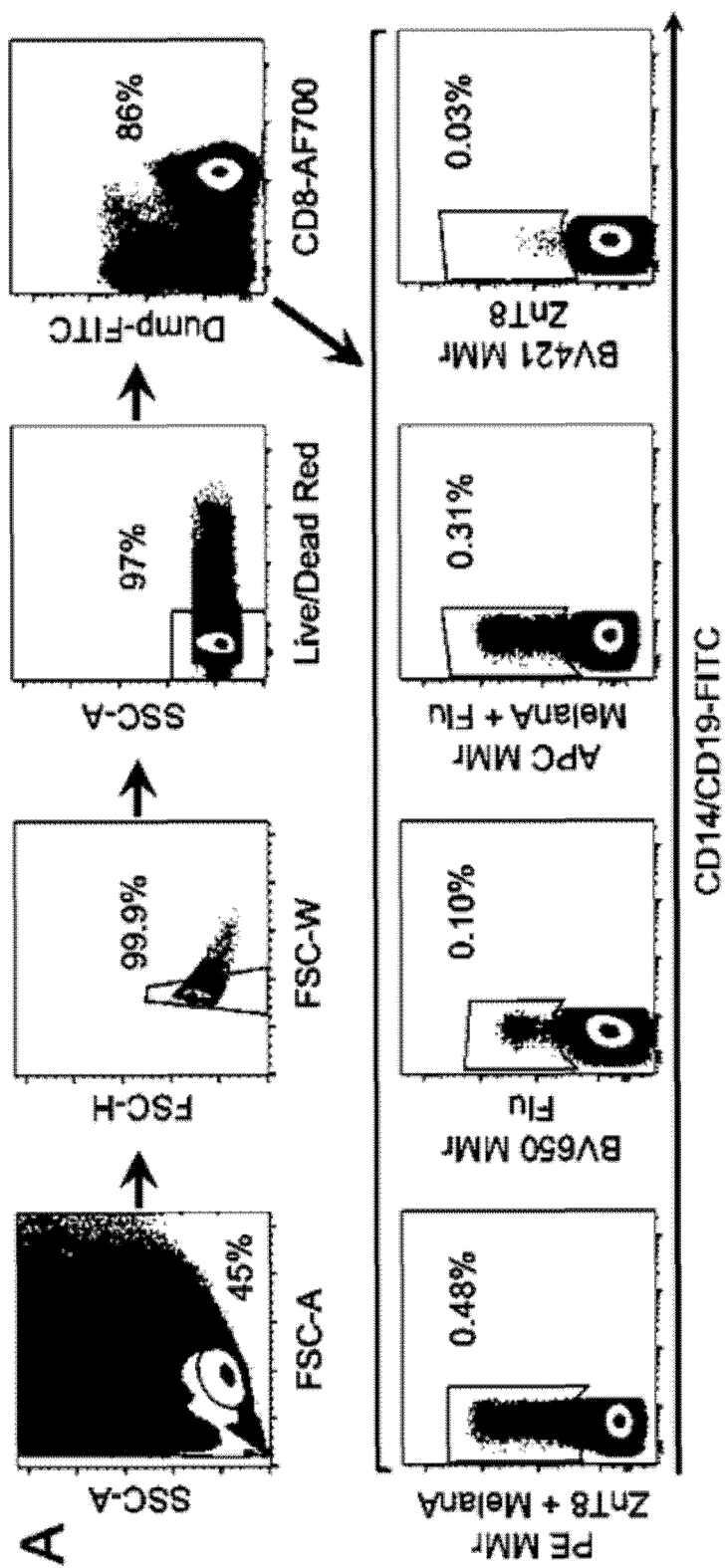

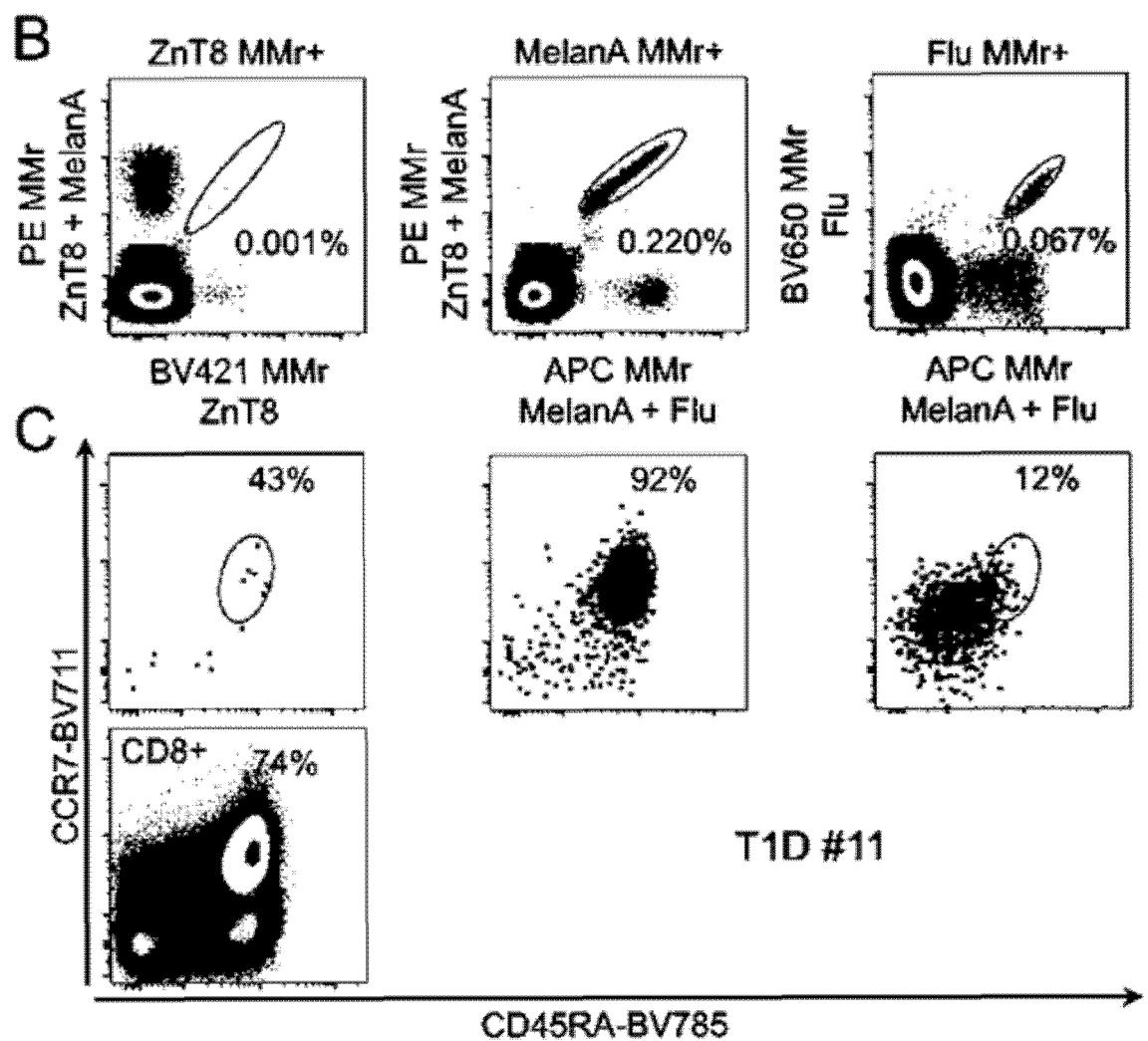
Figures 2B-C

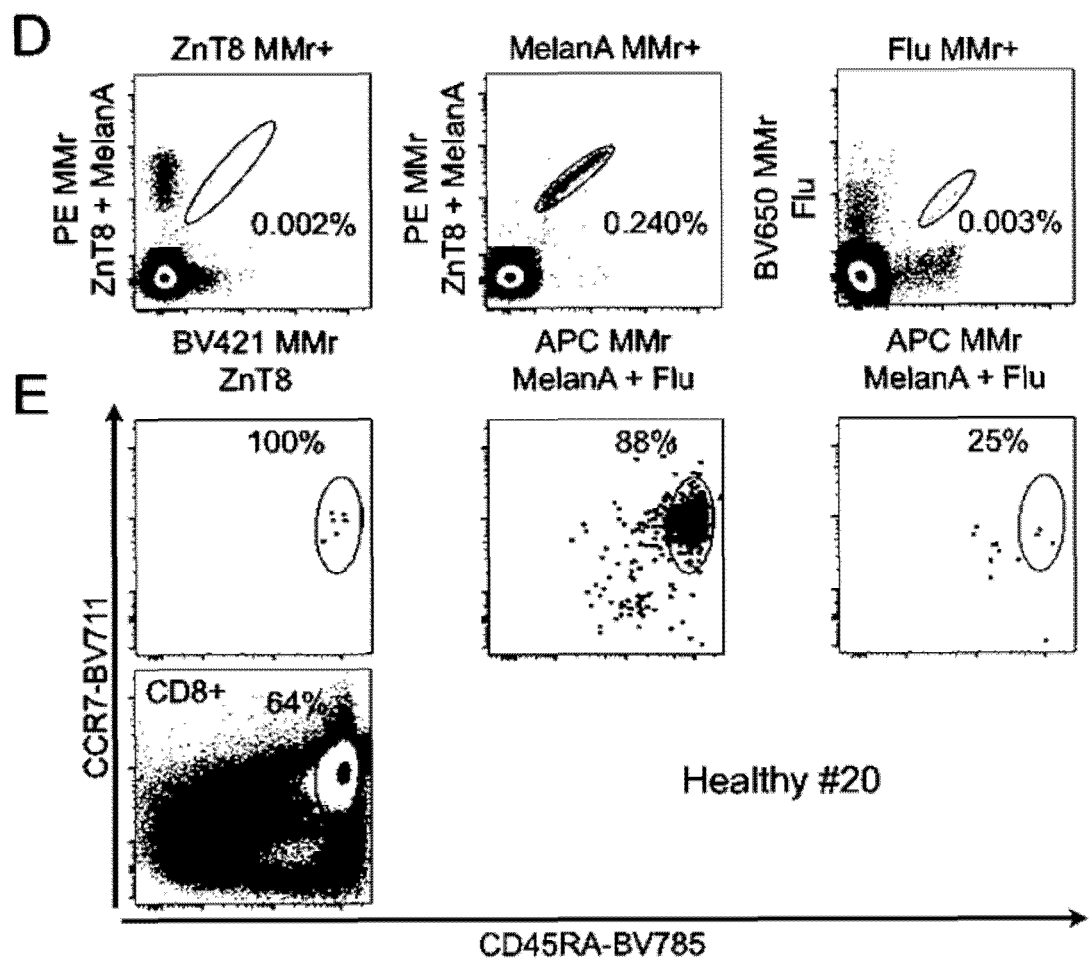
Figures 2D-E

| Status | Donor | Age (years) | Gender | Sort strategy | Sorted wells | Growing wells | ZnT8 MMr+ wells | Cloning efficiency | Clones |
|---|---|---|---|---|---|---|---|---|---|
| T1D | D222D | 60 | M | In vitro | 100 | 5 | 3 | 3% | (1), 2, 3 |
| T1D | D010R | 12 | M | Ex vivo | 50 | 10 | 2 | 4% | 1D3, (1E2) |
| H | H017N | 32 | F | In vitro | 80 | 8 | 1 | 1% | A1 |
| H | H314C | 22 | M | Ex vivo | 60 | 2 | 1 | 2% | 6C4 |
| H | H328C | 28 | M | Ex vivo | 45 | 12 | 0 | 0% | NA |
| | | | | In vitro | 119 | 26 | 3 | 2% | 8E8, 9C8, (9B3) |

Figure 7A

| T cell of origin | TCR chain | CDR3 sequence | V(D)J genes | SEQ ID: |
|---|---|---|---|---|
| D222D 1, 2, 3 | β | C A S S I E G P T G E L F<br>tgtgccagtagtatagaggggcccaccggggagctgttt | TRBV19*01<br>TRBD1*01<br>TRBJ2-2*01 | 1 |
| | α | C A V T G A N N L F F<br>tgtgcggtaactggggcaaacaacctcttcttt | TRAV17*01<br>TRAJ36*01 | 2 |
| D010R 1E2 | β | C A S G G S S Y E Q Y F<br>tgtgccagcggggaagctcctacgagcagtacttc | TRBV19*01<br>TRBD2*01<br>TRBJ2-7*01 | 3 |
| | α | C A G T R N N L F F<br>tgtgctggaacgcgaaacaacctcttcttt | TRAV35*02<br>TRAJ36*01 | 4 |
| D010R 12B4 | β | C A S T G L A G T Q Y F<br>tgtgccagtacgggactagcgggaacgcagtatttt | TRBV19*01<br>TRBD2*02<br>TRBJ2-3*01 | 5 |
| | α | C A V D N Y G Q N F V F<br>tgtgctgtg gataactatggtcagaattttgtcttt | TRAV1-2*01<br>TRAJ26*01 | 6 |
| D010R 1D3 | β | C A S S S V G V D T Q Y F<br>tgtgccagcagctctgtggggtagatacgcagtatttt | TRBV6-1*01<br>TRBD1*01<br>TRBJ2-3*01 | 7 |
| | α | C A G G S N D Y K L S F<br>tgtgcagggggctctaacgactacaagctcagcttt | TRAV25*01<br>TRAJ20*01 | 8 |
| D027H 11F4 | β | C A S S Y S P G D Y E Q Y F<br>tgtgccagcagttactcgccggggactacgagcagtacttc | TRBV6-2*01<br>/6-3*01<br>TRBD2*01<br>TRBJ2-7*01 | 9 |
| | α | C A P G V I S S G S A R Q L T F<br>tgtgctcctgggggtcataagttctggttctgcaaggcaactgaccttt | TRDV1*01<br>TRAJ22*01 | 10 |
| | α | C A V A G A G S Y Q L T F<br>tgtgccgttgctggggctgggagttaccaactcactttc | TRAV12-2*01<br>TRAJ28*01 | 11 |
| D027H 6E4 | β | C A S S Q F P G G S T E A F F<br>tgcgccagcagccaattccccggggggagcactgaagctttcttt | TRBV4-1*01<br>TRBD2*01<br>TRBJ1-1*01 | 12 |
| | α | C A E N I P T S G T Y K Y I F<br>tgtgcagagaatattcctacctcaggaacctacaaatacatcttt | TRAV13-2*01<br>TRAJ40*01 | 13 |

Figure 11

| T cell of origin | TCR chain | CDR3 sequence | V(D)J genes | SEQ ID: |
|---|---|---|---|---|
| H017N A1 | β | C A S S P S W L S G V T Q Y F<br>tgtgccagcagccctcctggctttctggggttacgcagtatttt | TRBV7-2*02<br>TRBD1*01<br>TRBJ2-3*01 | 14 |
| | α | C A V D M G N T P L V F<br>tgtgccgtggacatgggaaacacacctcttgtcttt | TRAV39*01<br>TRAJ29*01 | 15 |
| H314C 6C4 | β | C A S Q S Y R V G S E Q Y F<br>tgtgccagtcagagttacagggtggggtccgagcagtacttc | TRBV6-5*01<br>TRBD1*01<br>TRBJ2-7*01 | 16 |
| | α | C L L M E Y G N K L V F<br>tgtctcctcatggaatatggaaacaagctggtctttt | TRAV40*01<br>TRAJ47*02 | 17 |
| | α | C A F F P Y G Q N F V F<br>tgtgcttttttttccttatggtcagaattttgtcttt | TRAV38-2<br>TRAJ26*01 | 18 |
| H328C 8E8 | β | C A S S Q E G T A Y E Q Y F<br>tgtgccagcagccaagagggacagcctacgagcagtacttc | TRBV4-2*01<br>TRBD1*01<br>TRBJ2-7*01 | 19 |
| | α | C A A S G T L T T S G T Y K Y I F<br>tgtgcagcaagtggaaccctaactacctcaggaacctacaaatacatcttt | TRAV29*01<br>TRAJ40*01 | 20 |
| H328C 9B3 | β | C A S S P W T G I P Y N S P L H F<br>tgtgccagcagcccgtggacagggatcccctataattcacccctccacttt | TRBV9*01<br>TRBD1*01<br>TRBJ1-6*02 | 21 |
| | α | C A V V R T Q G G S E K L V F<br>tgtgctgttgtcagaactcagggcggatctgaaaagctggtcttt | TRAV21*01<br>TRAJ57*01 | 22 |
| H328C 9C8 | β | C A S S E V Q G F N G Y T F<br>tgtgccagcagtgaagtgggacagggatttaatggctacaccttc | TRBV25-1*01<br>TRBD1*01<br>TRBJ1-2*01 | 23 |
| | α | C A G I L S Y G Q N F V F<br>tgtgcaggcattctctcctatggtcagaattttgtcttt | TRAV25*01<br>TRAJ26*01 | 24 |

Figure 12

Figure 13

SEQUENCE LISTING

```
<160> NUMBER OF SEQ ID NOS: 48

<210> SEQ ID NO 1
<211> LENGTH: 13
<212> TYPE: PRT
<213> ORGANISM: Homo sapiens

<400> SEQUENCE: 1

Cys Ala Ser Ser Ile Glu Gly Pro Thr Gly Glu Leu Phe
1               5                   10

<210> SEQ ID NO 2
<211> LENGTH: 11
<212> TYPE: PRT
<213> ORGANISM: Homo sapiens

<400> SEQUENCE: 2

Cys Ala Val Thr Gly Ala Asn Asn Leu Phe Phe
1               5                   10

<210> SEQ ID NO 3
<211> LENGTH: 12
<212> TYPE: PRT
<213> ORGANISM: Homo sapiens

<400> SEQUENCE: 3

Cys Ala Ser Gly Gly Ser Ser Tyr Glu Gln Tyr Phe
1               5                   10

<210> SEQ ID NO 4
```

```
<211> LENGTH: 10
<212> TYPE: PRT
<213> ORGANISM: Homo sapiens

<400> SEQUENCE: 4

Cys Ala Gly Thr Arg Asn Asn Leu Phe Phe
1               5                   10

<210> SEQ ID NO 5
<211> LENGTH: 12
<212> TYPE: PRT
<213> ORGANISM: Homo sapiens

<400> SEQUENCE: 5

Cys Ala Ser Thr Gly Leu Ala Gly Thr Gln Tyr Phe
1               5                   10

<210> SEQ ID NO 6
<211> LENGTH: 12
<212> TYPE: PRT
<213> ORGANISM: Homo sapiens

<400> SEQUENCE: 6

Cys Ala Val Asp Asn Tyr Gly Gln Asn Phe Val Phe
1               5                   10

<210> SEQ ID NO 7
<211> LENGTH: 13
<212> TYPE: PRT
<213> ORGANISM: Homo sapiens

<400> SEQUENCE: 7

Cys Ala Ser Ser Ser Val Gly Val Asp Thr Gln Tyr Phe
1               5                   10

<210> SEQ ID NO 8
<211> LENGTH: 12
<212> TYPE: PRT
<213> ORGANISM: Homo sapiens

<400> SEQUENCE: 8

Cys Ala Gly Gly Ser Asn Asp Tyr Lys Leu Ser Phe
1               5                   10

<210> SEQ ID NO 9
<211> LENGTH: 14
<212> TYPE: PRT
<213> ORGANISM: Homo sapiens

<400> SEQUENCE: 9

Cys Ala Ser Ser Tyr Ser Pro Gly Asp Tyr Glu Gln Tyr Phe
1               5                   10

<210> SEQ ID NO 10
<211> LENGTH: 16
<212> TYPE: PRT
<213> ORGANISM: Homo sapiens

<400> SEQUENCE: 10

Cys Ala Pro Gly Val Ile Ser Ser Gly Ser Ala Arg Gln Leu Thr Phe
1               5                   10                  15

<210> SEQ ID NO 11
<211> LENGTH: 13
<212> TYPE: PRT
```

<213> ORGANISM: Homo sapiens

<400> SEQUENCE: 11

Cys Ala Val Ala Gly Ala Gly Ser Tyr Gln Leu Thr Phe
1               5                   10

<210> SEQ ID NO 12
<211> LENGTH: 15
<212> TYPE: PRT
<213> ORGANISM: Homo sapiens

<400> SEQUENCE: 12

Cys Ala Ser Ser Gln Phe Pro Gly Gly Ser Thr Glu Ala Phe Phe
1               5                   10                  15

<210> SEQ ID NO 13
<211> LENGTH: 15
<212> TYPE: PRT
<213> ORGANISM: Homo sapiens

<400> SEQUENCE: 13

Cys Ala Glu Asn Ile Pro Thr Ser Gly Thr Tyr Lys Tyr Ile Phe
1               5                   10                  15

<210> SEQ ID NO 14
<211> LENGTH: 15
<212> TYPE: PRT
<213> ORGANISM: Homo sapiens

<400> SEQUENCE: 14

Cys Ala Ser Ser Pro Ser Trp Leu Ser Gly Val Thr Gln Tyr Phe
1               5                   10                  15

<210> SEQ ID NO 15
<211> LENGTH: 12
<212> TYPE: PRT
<213> ORGANISM: Homo sapiens

<400> SEQUENCE: 15

Cys Ala Val Asp Met Gly Asn Thr Pro Leu Val Phe
1               5                   10

<210> SEQ ID NO 16
<211> LENGTH: 14
<212> TYPE: PRT
<213> ORGANISM: Homo sapiens

<400> SEQUENCE: 16

Cys Ala Ser Gln Ser Tyr Arg Val Gly Ser Glu Gln Tyr Phe
1               5                   10

<210> SEQ ID NO 17
<211> LENGTH: 12
<212> TYPE: PRT
<213> ORGANISM: Homo sapiens

<400> SEQUENCE: 17

Cys Leu Leu Met Glu Tyr Gly Asn Lys Leu Val Phe
1               5                   10

<210> SEQ ID NO 18
<211> LENGTH: 12
<212> TYPE: PRT
<213> ORGANISM: Homo sapiens -continued

<400> SEQUENCE: 18

Cys Ala Phe Phe Pro Tyr Gly Gln Asn Phe Val Phe
1               5                   10

<210> SEQ ID NO 19
<211> LENGTH: 14
<212> TYPE: PRT
<213> ORGANISM: Homo sapiens

<400> SEQUENCE: 19

Cys Ala Ser Ser Gln Glu Gly Thr Ala Tyr Glu Gln Tyr Phe
1               5                   10

<210> SEQ ID NO 20
<211> LENGTH: 17
<212> TYPE: PRT
<213> ORGANISM: Homo sapiens

<400> SEQUENCE: 20

Cys Ala Ala Ser Gly Thr Leu Thr Thr Ser Gly Thr Tyr Lys Tyr Ile
1               5                   10                  15

Phe

<210> SEQ ID NO 21
<211> LENGTH: 17
<212> TYPE: PRT
<213> ORGANISM: Homo sapiens

<400> SEQUENCE: 21

Cys Ala Ser Ser Pro Trp Thr Gly Ile Pro Tyr Asn Ser Pro Leu His
1               5                   10                  15

Phe

<210> SEQ ID NO 22
<211> LENGTH: 15
<212> TYPE: PRT
<213> ORGANISM: Homo sapiens

<400> SEQUENCE: 22

Cys Ala Val Val Arg Thr Gln Gly Gly Ser Glu Lys Leu Val Phe
1               5                   10                  15

<210> SEQ ID NO 23
<211> LENGTH: 15
<212> TYPE: PRT
<213> ORGANISM: Homo sapiens

<400> SEQUENCE: 23

Cys Ala Ser Ser Glu Val Gly Gln Gly Phe Asn Gly Tyr Thr Phe
1               5                   10                  15

<210> SEQ ID NO 24
<211> LENGTH: 13
<212> TYPE: PRT
<213> ORGANISM: Homo sapiens

<400> SEQUENCE: 24

Cys Ala Gly Ile Leu Ser Tyr Gly Gln Asn Phe Val Phe
1               5                   10

<210> SEQ ID NO 25
<211> LENGTH: 39
<212> TYPE: DNA

<213> ORGANISM: Homo sapiens

<400> SEQUENCE: 25
tgtgccagta gtatagaggg gcccaccggg gagctgttt                          39

<210> SEQ ID NO 26
<211> LENGTH: 33
<212> TYPE: DNA
<213> ORGANISM: Homo sapiens

<400> SEQUENCE: 26
tgtgcggtaa ctggggcaaa caacctcttc ttt                                33

<210> SEQ ID NO 27
<211> LENGTH: 36
<212> TYPE: DNA
<213> ORGANISM: Homo sapiens

<400> SEQUENCE: 27
tgtgccagcg ggggaagctc ctacgagcag tacttc                             36

<210> SEQ ID NO 28
<211> LENGTH: 30
<212> TYPE: DNA
<213> ORGANISM: Homo sapiens

<400> SEQUENCE: 28
tgtgctggaa cgcgaaacaa cctcttcttt                                    30

<210> SEQ ID NO 29
<211> LENGTH: 36
<212> TYPE: DNA
<213> ORGANISM: Homo sapiens

<400> SEQUENCE: 29
tgtgccagta cgggactagc gggaacgcag tatttt                             36

<210> SEQ ID NO 30
<211> LENGTH: 36
<212> TYPE: DNA
<213> ORGANISM: Homo sapiens

<400> SEQUENCE: 30
tgtgctgtgg ataactatgg tcagaatttt gtcttt                             36

<210> SEQ ID NO 31
<211> LENGTH: 39
<212> TYPE: DNA
<213> ORGANISM: Homo sapiens

<400> SEQUENCE: 31
tgtgccagca gctctgtggg ggtagatacg cagtatttt                          39

<210> SEQ ID NO 32
<211> LENGTH: 36
<212> TYPE: DNA
<213> ORGANISM: Homo sapiens

<400> SEQUENCE: 32
tgtgcagggg gctctaacga ctacaagctc agcttt                             36

<210> SEQ ID NO 33
<211> LENGTH: 42

```
<212> TYPE: DNA
<213> ORGANISM: Homo sapiens

<400> SEQUENCE: 33
tgtgccagca gttactcgcc gggggactac gagcagtact tc                          42

<210> SEQ ID NO 34
<211> LENGTH: 48
<212> TYPE: DNA
<213> ORGANISM: Homo sapiens

<400> SEQUENCE: 34
tgtgctcctg gggtcataag ttctggttct gcaaggcaac tgacctttt                   48

<210> SEQ ID NO 35
<211> LENGTH: 39
<212> TYPE: DNA
<213> ORGANISM: Homo sapiens

<400> SEQUENCE: 35
tgtgccgttg ctggggctgg gagttaccaa ctcactttc                              39

<210> SEQ ID NO 36
<211> LENGTH: 45
<212> TYPE: DNA
<213> ORGANISM: Homo sapiens

<400> SEQUENCE: 36
tgcgccagca gccaattccc cgggggagc actgaagctt tcttt                        45

<210> SEQ ID NO 37
<211> LENGTH: 45
<212> TYPE: DNA
<213> ORGANISM: Homo sapiens

<400> SEQUENCE: 37
tgtgcagaga atattcctac ctcaggaacc tacaaataca tcttt                       45

<210> SEQ ID NO 38
<211> LENGTH: 45
<212> TYPE: DNA
<213> ORGANISM: Homo sapiens

<400> SEQUENCE: 38
tgtgccagca gcccctcctg gctttctggg gttacgcagt atttt                       45

<210> SEQ ID NO 39
<211> LENGTH: 36
<212> TYPE: DNA
<213> ORGANISM: Homo sapiens

<400> SEQUENCE: 39
tgtgccgtgg acatgggaaa cacacctctt gtcttt                                 36

<210> SEQ ID NO 40
<211> LENGTH: 42
<212> TYPE: DNA
<213> ORGANISM: Homo sapiens

<400> SEQUENCE: 40
tgtgccagtc agagttacag ggtggggtcc gagcagtact tc                          42

<210> SEQ ID NO 41
```

```
<211> LENGTH: 36
<212> TYPE: DNA
<213> ORGANISM: Homo sapiens

<400> SEQUENCE: 41
tgtctcctca tggaatatgg aaacaagctg gtcttt                                36

<210> SEQ ID NO 42
<211> LENGTH: 36
<212> TYPE: DNA
<213> ORGANISM: Homo sapiens

<400> SEQUENCE: 42
tgtgcttttt ttccttatgg tcagaatttt gtcttt                                36

<210> SEQ ID NO 43
<211> LENGTH: 42
<212> TYPE: DNA
<213> ORGANISM: Homo sapiens

<400> SEQUENCE: 43
tgtgccagca gccaagaggg gacagcctac gagcagtact tc                         42

<210> SEQ ID NO 44
<211> LENGTH: 51
<212> TYPE: DNA
<213> ORGANISM: Homo sapiens

<400> SEQUENCE: 44
tgtgcagcaa gtggaaccct aactacctca ggaacctaca aatacatctt t               51

<210> SEQ ID NO 45
<211> LENGTH: 51
<212> TYPE: DNA
<213> ORGANISM: Homo sapiens

<400> SEQUENCE: 45
tgtgccagca gcccgtggac agggatcccc tataattcac ccctccactt t               51

<210> SEQ ID NO 46
<211> LENGTH: 45
<212> TYPE: DNA
<213> ORGANISM: Homo sapiens

<400> SEQUENCE: 46
tgtgctgttg tcagaactca gggcggatct gaaaagctgg tcttt                      45

<210> SEQ ID NO 47
<211> LENGTH: 45
<212> TYPE: DNA
<213> ORGANISM: Homo sapiens

<400> SEQUENCE: 47
tgtgccagca gtgaagtggg acagggattt aatggctaca ccttc                      45

<210> SEQ ID NO 48
<211> LENGTH: 39
<212> TYPE: DNA
<213> ORGANISM: Homo sapiens

<400> SEQUENCE: 48
tgtgcaggca ttctctccta tggtcagaat tttgtcttt                             39
```

T CELL RECEPTORS (TCR) AND USES THEREOF FOR THE DIAGNOSIS AND TREATMENT OF DIABETES

FIELD OF THE INVENTION

The present invention relates to T-cell receptors (TCR) that recognize pancreatic beta-cell epitopes and uses thereof for the diagnosis and treatment of diabetes.

BACKGROUND OF THE INVENTION

T cells are key actors on the stage of pancreatic insulitis that is pathognomonic of type 1 diabetes (T1D). $CD8^+$ T cells, in particular, are the final mediators of islet destruction, both in non-obese diabetic (NOD) mice and in patients (1). Indeed, preproinsulin (PPI)-reactive $CD8^+$ T cell clones are capable of lysing β cells in vitro (2,3) and islet antigen (Ag)-specific $CD8^+$ T cells are found in the insulitis infiltrates of T1D patients (4). Hence, the interest for studying autoimmune T cells has grown steadily, as they can provide biomarkers for disease staging complementary to autoantibodies (aAbs) (5) and have proven useful to monitor T-cell modifications induced in immunotherapeutic trials (6,7). The preliminary step towards this goal has been to investigate whether detection of islet-reactive T cells allows distinction of T1D patients from healthy subjects. This is the case when analyzing interferon (IFN)-γ-secreting $CD8^+$ T cells by enzyme-linked immunospot (ELISpot) (8), which excludes most naïve and regulatory T cells, which are poorly activated upon the short-term ELISpot stimulation (9). The situation is different when using HLA Class I multimers (MMrs), which detect islet-reactive $CD8^+$ T cells independently of their functional profile. $MMr^+CD8^+$ T cells were frequently (10, 12), although not invariably (13, 14), found at similar frequencies in both T1D and healthy subjects, but they exhibited differential phenotypes, i.e. memory vs. naïve (10) or effector vs. regulatory (14) in T1D and healthy subjects, respectively. Similar pictures have been described for autoreactive $CD4^+$ T cells (15, 16). The mechanisms underlying this 'benign' autoimmunity in healthy individuals have however remained elusive. Likewise, the considerable heterogeneity of the $CD8^+$ T-cell epitope cartography, which has been extensively studied for the most common HLA-A2 (HLA-A*02:01) restriction, remains poorly understood. The reactivities found in T1D patients are quite heterogeneous, as each of the β-cell epitopes identified is recognized by no more than half of all HLA-A2$^+$ new-onset T1D patients, with $GAD_{114-123}$ (8, 17) and $PPI_{15-24}$ (2) ranking the highest. We recently reported a notable exception for the β-cell Ag zinc transporter (ZnT)8, which harbors an immunodominant $ZnT8_{186-194}$ epitope targeted by more than 70% of HLA-A2$^+$ new-onset T1D patients, children and adults alike (18).

SUMMARY OF THE INVENTION

The present invention relates to T-cell receptors (TCR) that recognize pancreatic beta-cell epitopes and uses thereof for the diagnosis and treatment of diabetes. In particular, the present invention is defined by the claims.

DETAILED DESCRIPTION OF THE INVENTION

Among the β-cell antigens recognized by autoreactive $CD8^+$ T cells in type 1 diabetes (T1D), the $ZnT8_{185-194}$ epitope was found to be targeted in a high proportion of HLA-A2$^+$ patients. The inventors aimed to investigate the reasons of this unprecedented immunodominance. Using HLA-A2 multimers, $ZnT8_{185-194}$-specific $CD8^+$ T cells could be detected at similar frequencies in both T1D and healthy children, but featured markers of prior in vivo priming only in T1D children. These $CD8^+$ T cells displayed high antigen avidity and cytotoxic activity against cells when isolated from T1D patients, which correlated with selection of a skewed T-cell receptor (TCR) repertoire. Such high avidity is an unusual feature for autoreactive T cells and was associated with virtual absence of ZnT8 expression in human thymic medullary epithelial cells, thus exempting the $ZnT8_{185-194}$ region from central tolerance. This favors the escape of cognate naïve T-cell precursors and their subsequent peripheral priming in T1D patients. $ZnT8_{185-194}$ may be the prototype of a more generalized autoimmune mechanism involving other β-cell epitopes, leading to the emergence of immunodominant T cells amenable to biomarker development and therapeutic targeting.

As used herein, the term "TCR" has its general meaning in the art and refers to the molecule found on the surface of T cells that is responsible for recognizing antigens bound to MHC molecules. During antigen processing, antigens are degraded inside cells and then carried to the cell surface in the form of peptides bound to major histocompatibility complex (MHC) molecules (human leukocyte antigen or HLA molecules in humans). T cells are able to recognize these peptide-MHC complex at the surface of professional antigen presenting cells or target tissue cells such as β cells in T1D. There are two different classes of MHC molecules: MHC Class I and MHC Class II that deliver peptides from different cellular compartments to the cell surface that are recognized by CD8+ and CD4+ T cells, respectively. The T cell receptor or TCR is the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. Each chain of the TCR is a member of the immunoglobulin superfamily and possesses one N-terminal immunoglobulin (Ig)-variable (V) domain, one Ig-constant (C) domain, a transmembrane region, and a short cytoplasmic tail at the C-terminal end. The constant domain of the TCR consists of short connecting sequences in which a cysteine residue forms a disulfide bond, making a link between the two chains. The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3 chains, together with the TCR, form what is known as the TCR complex. The signal from the TCR complex is enhanced by simultaneous binding of the MHC molecules by a specific co-receptor. On helper T cells, this co-receptor is CD4 (specific for class II MHC); whereas on cytotoxic T cells, this co-receptor is CD8 (specific for class I MHC). The co-receptor not only ensures the specificity of the TCR for an antigen, but also allows prolonged engagement between the antigen presenting cell and the T cell and recruits essential molecules (e.g., LCK) inside the cell involved in the signaling of the activated T lymphocyte. The term "T-cell receptor" is thus used in the conventional sense to mean a molecule capable of recognising a peptide when presented by an MHC molecule. The molecule may be a heterodimer of two chains α and β (or optionally γ and δ) or it may be a recombinant single chain TCR construct. The variable domain of both the TCR α-chain and β-chain have three hypervariable or complementarity determining regions (CDRs). CDR3 is the main CDR responsible for recognizing processed antigen. Its hypervariability is determined by recombination events that bring together segments from different gene loci carrying several possible alleles. The genes involved are V and J for the TCR α-chain and V, D and J for the TCR β-chain. Further amplifying the diversity of this CDR3 domain, random nucleotide deletions and additions during recombination take place at the junction of V-J for TCR α-chain, thus giving rise to V(N)J sequences; and V-D and D-J for TCR β-chain, thus giving rise to V(N)D(N)J sequences. Thus, the number of possible CDR3 sequences generated is immense and accounts for the wide capability of the whole TCR repertoire to recognize a number of disparate antigens. At the same time, this CDR3 sequence constitutes a specific molecular fingerprint for its corresponding T cell. The CDR3 amino acid and nucleotide sequences of the TCR characterized by the inventors are listed in the following Table A. Rearranged nucleotide sequences are presented as V segments (underlined) followed by (ND)N segments (not underlined; N additions denoted in bold) and then by J segments (underlined), as annotated using the IMGT database (www.imgt.org).

TABLE A

CDR3 amino acid and nucleotide sequence of the TCR identified by the inventors

| T cell of origin | TCR chain | CDR3 sequence | V(D)J genes | SEQ ID |
|---|---|---|---|---|
| D222D 1, 2, 3 | β | C A S S E E G P T G E L F<br>tgtgccagtagtatagagggggcccaccggggagctgttt | TRBV19*01<br>TRBD1*01<br>TRBJ2-2*01 | 1 |
|  | α | C A V T G A N N L F F<br>tgtgcggtaactggggcaaacaacctcttcttt | TRAV17*01<br>TRAJ36*01 | 2 |
| D010R 1E2 | β | C A S G G S S Y E Q Y F<br>tgtgccagcggggaaagctcctacgagcagtacttc | TRBV19*01<br>TRBD2*01<br>TRBJ2-7*01 | 3 |
|  | α | C A G T R N N L F F<br>tgtgctggaacgcgaaacaacctcttcttt | TRAV35*02<br>TRAJ36*01 | 4 |
| D010R 12B4 | β | C A S T G L A G T Q Y F<br>tgtgccagtacgggactagcgggaacgcagtatttt | TRBV19*01<br>TRBD2*02<br>TRBJ2-3*01 | 5 |
|  | α | C A V D N Y G Q N F V F<br>tgtgctgtg gataactatggtcagaattttgtcttt | TRAV1-2*01<br>TRAJ26*01 | 6 |
| D101R 1D3 | β | C A S S S V G V D T Q Y F<br>tgtgccagcagctctgtgggggtagatacgcagtatttt | TRBV6-1*01<br>TRBD1*01<br>TRBJ2-3*01 | 7 |
|  | α | C A G G S N D Y K L S F<br>tgtgcagggggctctaacgactacaagctcagcttt | TRAV25*01<br>TRAJ20*01 | 8 |
| D027H 11F4 | β | C A S S Y S P G D Y E Q Y F<br>tgtgccagcagttactcgccgggggactacgagcagtacttc | TRBV6-2*01/<br>6-3*01<br>TRBD2*01<br>TRBJ2-7*01 | 9 |
|  | α | C A P G V I S S G S A R Q L T F<br>tgtgctcctggggtcataagttctggttctgcaaggcaactgaccttt | TRDV1*01<br>TRAJ22*01 | 10 |
|  | α | C A V A G A G S Y Q L T F<br>tgtgccgttgctggggctgggagttaccaactcactttc | TRAV12-2*01<br>TRAJ28*01 | 11 |
| D027H 6E4 | β | C A S S Q F P G G S T E A F F<br>tgcgccagcagccaattccccggggggagcactgaagctttcttt | TRBV4-1*01<br>TRBD2*01<br>TRBJ1-1*01 | 12 |
|  | α | C A E N I P T S G T Y K Y I F<br>tgtgcagagaatattcctacctcaggaacctacaaatacatcttt | TRAV13-2*01<br>TRAJ40*01 | 13 |
| H017N A1 | β | C A S S P S W L S G V T Q Y F<br>tgtgccagcagcccctcctggctttctggggttacgcagtatttt | TRAB7-2*02<br>TRBD1*01<br>TRBJ2-3*01 | 14 |
|  | α | C A V D M G N T P L V F<br>tgtgccgtggacatgggaaacacacctcttgtcttt | TRAV39*01<br>TRAJ29*01 | 15 |
| H314C 64C | β | C A S Q S Y R V G S E Q Y F<br>tgtgccagtcagagttacagggtggggtccgagcagtacttc | TRBV6-5*01<br>TRBD1*01<br>TRBJ2*01 | 16 |

TABLE A-continued

CDR3 amino acid and nucleotide sequence
of the TCR identified by the inventors

| T cell of origin | TCR chain | CDR3 sequence | V(D)J genes | SEQ ID |
|---|---|---|---|---|
| | α | C L L M E Y G N K L V F<br>tgtctcctcatggaatatggaaacaagctggtctttt | TRAV40*01<br>TRAJ47*02 | 17 |
| | α | C A F F P Y G Q N F V F<br>tgtgcttttttttcctatggtcagaatttttgtctttt | TRAV38-2<br>TRAJ26*01 | 18 |
| H328C 8E8 | β | C A S S Q E G T A Y E Q Y F<br>tgtgccagcagccaagagggacagcctacgagcagtacttc | TRBV4-2*01<br>TRBD1*01<br>TRBJ2-7*01 | 19 |
| | α | C A A S G T L T T S G T Y K Y I F<br>tgtgcagcaagtggaaccctaactacctcaggaacctacaaatacatctttt | TRAV28*01<br>TRAJ40*01 | 20 |
| H328C 9B3 | β | C A S S P W T G I P Y N S P L H F<br>tgtgccagcagcccgtggacagggatccctataattcacccctccactttt | TRBV9*01<br>TRBD1*01<br>TRBJ1-6*02 | 21 |
| | α | C A V V R T Q G G S E K L V F<br>tgtgctgttgtcagaactcagggcggatctgaaaagctggtctttt | TRAV21*01<br>TRAJ57*01 | 22 |
| H328C 9C8 | β | C A S S E V G Q G F N G Y T F<br>tgtgccagcagtgaagtgggacagggatttaatggctacaccttc | TRBV25-1*01<br>TRBD1*01<br>TRBJ1-2*01 | 23 |
| | α | C A G I L S Y G Q N F V F<br>tgtgcaggcattctctcctatggtcagaatttttgtctttt | TRAV25*01<br>TRAJ26*01 | 24 |

In some embodiments, the TCR of the present invention comprises an α chain and a β chain, wherein the β chain and α chain CDR3 sequences consists of the amino acid sequences having at least 90% of identity with SEQ ID NO:1 and SEQ ID NO:2 respectively.

In some embodiments, the TCR of the present invention comprises a β chain and an α chain, wherein the α chain and β chain CDR3 sequences consists of the amino acid sequences having at least 90% of identity with SEQ ID NO:3 and SEQ ID NO:4 respectively.

In some embodiments, the TCR of the present invention comprises a β chain and an α chain, wherein the α chain and β chain CDR3 sequences consists of the amino acid sequences having at least 90% of identity with SEQ ID NO:5 and SEQ ID NO:6 respectively.

In some embodiments, the TCR of the present invention comprises a β chain and an α chain, wherein the α chain and β chain CDR3 sequences consists of the amino acid sequences having at least 90% of identity with SEQ ID NO:7 and SEQ ID NO:8 respectively.

In some embodiments, the TCR of the present invention comprises a β chain and an α chain, wherein the α chain and β chain CDR3 sequences consists of the amino acid sequences having at least 90% of identity with SEQ ID NO:9 and SEQ ID NO:10 or SEQ ID NO:11 respectively.

In some embodiments, the TCR of the present invention comprises a β chain and an α chain, wherein the α chain and β chain CDR3 sequences consists of the amino acid sequences having at least 90% of identity with SEQ ID NO:12 and SEQ ID NO:13 respectively.

In some embodiments, the TCR of the present invention comprises a β chain and an α chain, wherein the α chain and β chain CDR3 sequences consists of the amino acid sequences having at least 90% of identity with SEQ ID NO:14 and SEQ ID NO:15 respectively.

In some embodiments, the TCR of the present invention comprises a β chain and an α chain, wherein the α chain and β chain CDR3 sequences consists of the amino acid sequences having at least 90% of identity with SEQ ID NO:16 and SEQ ID NO:17 or SEQ ID NO 18 respectively.

In some embodiments, the TCR of the present invention comprises a β chain and an α chain, wherein the α chain and β chain CDR3 sequences consists of the amino acid sequences having at least 90% of identity with SEQ ID NO:19 and SEQ ID NO:20 respectively.

In some embodiments, the TCR of the present invention comprises a β chain and an α chain, wherein the α chain and β chain CDR3 sequences consists of the amino acid sequences having at least 90% of identity with SEQ ID NO:21 and SEQ ID NO:22 respectively.

In some embodiments, the TCR of the present invention comprises a β chain and an α chain, wherein the α chain and β chain CDR3 sequences consists of the amino acid sequences having at least 90% of identity with SEQ ID NO:23 and SEQ ID NO:24 respectively.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

A further object of the present invention relates to a nucleic acid sequence that encodes for the amino acid sequence of the α chain and/or the β chain of the present invention.

As used herein, the term "nucleic acid sequence" has its general meaning in the art and refers to a DNA or RNA sequence. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxymethyl) uracil, 5-fiuorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid sequence is selected from the group consisting of SEQ ID NO:25-48.

In some embodiments, the nucleic acid sequence of the present invention is included in a suitable vector, such as a plasmid, cosmid, episome, artificial chromosome, phage or a viral vector. Hence, a further object of the invention relates to a vector comprising a nucleic acid sequence of the present invention. Typically, the vector is a viral vector which is an adeno-associated virus (AAV), a retrovirus, bovine papilloma virus, an adenovirus, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences"", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is repressed? by an analyte, cofactor, regulatory protein, etc.), and "constitutive promoters".

A further object of the present invention relates to a cell which comprises a nucleic acid sequence of the present invention. In some embodiments, the cell expresses the T-cell receptor of the present invention.

In some embodiments, the cell is a T-cell. The cell may be derived from a T-cell isolated from a subject. The T-cell may be part of a mixed cell population isolated from the subject, such as a population of peripheral blood lymphocytes (PBL) or whole unfractionated blood. T cells within the PBL population may be activated by methods known in the art, such as using anti-CD3 and CD28 antibodies or antigen-specific stimulation with peptide-pulsed antigen presenting cells. The T-cell may be a CD4+ helper T cell or a CD8+ cytotoxic T cell. The cell may be in a mixed population of CD4+ helper T cells/CD8+ cytotoxic T cells. Polyclonal activation, for example using anti-CD3 antibodies optionally in combination with anti-CD28 antibodies or mitogens such as phytohemagglutinin together with suitable cytokine cocktails will trigger the proliferation of CD4+ and CD8+ T cells, but may also trigger the proliferation of CD4+CD25+ regulatory T-cells.

A further object of the present invention relates to a method of producing the cell of the present invention, which comprises the step of transfecting or transducing a cell in vitro or ex vivo with the vector of the present invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In some embodiments, TCR gene transfer into regulatory T cells (Tregs) is desirable as they can induce immune tolerance. As used herein, the term 'Treg' or 'T regulatory cell' denotes a T lymphocyte endowed with a given antigen specificity imprinted by the TCR it expresses and with regulatory properties defined by the ability to suppress the response of conventional T lymphocytes or other immune cells. Such responses are known in the art and include, but are not limited to, cytotoxic activity against antigen-presenting target cells and secretion of different cytokines. Different types of Tregs exist and include, but are not limited to: inducible and thymic-derived Tregs, as characterized by different phenotypes such as CD4+CD25+/high, CD4+ CD25+/highCD127-/low alone or in combination with additional markers that include, but are not limited to, FoxP3, neuropilin-1 (CD304), glucocorticoid-induced TNFR-related protein (GITR), cytotoxic T-lymphocyte-associated protein 4 (CTLA-4, CD152); T regulatory type 1 cells; T helper 3 cells. All these Tregs can be transformed with the TCR of the present invention either upon direct ex vivo purification or upon in vitro expansion or differentiation from different precursor cells. Examples of in vitro amplification protocols can be found in Battaglia et al., J. Immunol. 177:8338-8347 (2006), Putnam et al., Diabetes 58:652-662 (2009), Gregori et al., Blood 116:935-944 (2009). While methods for isolating or amplifying suitable numbers of polyclonal Tregs are well known in the art, isolation and/or in vitro expansion of Tregs specific for an antigen of interest such as a β-cell antigen yields more limited cell numbers. Thus, introduction of the desired antigen specificity by transfection or transduction of the β-cell antigen-reactive TCR of the present invention into polyclonal Tregs may be envisaged.

In some embodiments, the cell is isolated from a subject to whom the genetically modified cell is to be adoptively transferred. In some embodiments, a population of cells of the present invention are obtained by isolating a population of T-cells from a subject, optionally expanding said population of T cells in a population of regulatory T cells, and by subsequently proceeding with TCR gene transfer ex vivo and subsequent immunotherapy of the subject by adoptive transfer of the TCR-transduced cells. Alternatively, the population of cells is isolated from a different subject, such that it is allogeneic. In some embodiments, the population of cells is isolated from a donor subject. Alternatively the population of cells is, or is derived from, a population of stem cells, such as a haemopoietic stem cells (HSC). Gene transfer into HSCs does not lead to TCR expression at the cell surface, as stem cells do not express the CD3 molecules. However, when stem cells differentiate into lymphoid precursors that migrate to the thymus, the initiation of CD3 expression leads to the surface expression of the introduced TCR in thymocytes. An advantage of this approach is that the mature T cells, once produced, express only the introduced TCR and little or no endogenous TCR chains, because the expression of the introduced TCR chains suppresses rearrangement of endogenous TCR gene segments to form functional TCR alpha and beta genes. A further benefit is that the gene-modified stem cells are a continuous source of mature T-cells with the desired antigen specificity. The cell may therefore be a gene-modified stem cell, which, upon differentiation, produces a T-cell expressing a TCR of the present invention. The present invention also relates to a method of producing a T-cell expressing a TCR of the present invention by inducing the differentiation of a stem cell which comprises a nucleotide sequence of the present invention. Any carrier cell suitable for accepting the introduced TCR and expressing it in functional form can be used for research or therapeutic purposes. Further examples of such cells include, but are not limited to, Jurkat cells, T-cell hybridomas, lines or clones. All these cells may be expressing or not their endogenous TCRs.

The population of cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5\times10^3$/kg; and as high as $10^7$/kg, preferably $10^8$/kg. The number of cells will depend upon the ultimate use for which the composition is intended, as will the type of cells included therein. For example, if cells that are specific for a particular antigen are desired, then the population will contain greater than 70%, generally greater than 80%, 85% and 90-95% of such cells. The desired purity can be achieved by introducing a sorting step following introduction of the desired TCR sequence using methods such as HLA multimers and others known in the art. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

The cells of the present invention, in particular regulatory T cells or stem cells, are particularly suitable for the treatment of type 1 diabetes. According, a further object of the present invention relates to a method of treating type 1 diabetes in a subject in need thereof, comprising administering to the subject a therapeutically effective amount of a population of cells of the present invention.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By a "therapeutically effective amount" is meant a sufficient amount of cells generated with the present invention for the treatment of the disease at a reasonable benefit/risk ratio applicable to any medical treatment. It will be understood that the total usage of these cells will be decided by the attending physicians within the scope of sound medical judgment. The specific therapeutically effective dose level for any particular subject will depend upon a variety of factors including the age, body weight, general health, sex and diet of the subject; the time of administration, route of administration, and survival rate of the cells employed; the duration of the treatment; drugs used in combination or coincidental with the administered cells; and like factors well known in the medical arts. For example, it is well known within the skill of the art to start doses of cells at levels lower than those required to achieve the desired therapeutic effect and to gradually increase the dosage until the desired effect is achieved.

Typically, the population of cells of the present invention is administered to the subject in the form of pharmaceutical composition. The pharmaceutical composition may be produced by those of skill, employing accepted principles of treatment. Such principles are known in the art, and are set forth, for example, in Braunwald et al., eds., Harrison's Principles of Internal Medicine, 19th Ed., McGraw-Hill publisher, New York, N.Y. (2015), which is incorporated by reference herein. The pharmaceutical composition may be administered by any means that achieve their intended purpose. For example, administration may be by parenteral, subcutaneous, intravenous, intradermal, intramuscular, intraperitoneal, transdermal, or buccal routes. The pharmaceutical compositions may be administered parenterally by bolus injection or by gradual perfusion over time. The pharmaceutical compositions typically comprises suitable pharmaceutically acceptable carriers comprising excipients and auxiliaries which may facilitate processing of the active compounds into preparations which can be used pharmaceutically. The pharmaceutical compositions may contain from about 0.001 to about 99 percent, or from about 0.01 to about 95 percent of active compound(s), together with the excipient.

In some embodiments, the population of cells of the present invention may also find various applications in the research field. For example, the cells can be used as reagents, e.g. as 'surrogate' T cells to better characterize the TCR specificity, i.e. 1) its capability to induce responses of different kind such as cytotoxic responses and cytokine secretion; 2) its capability to bind HLA tetramers or multimers, as these cell reagents can be quite useful for standardization purposes; 3) its capability to recognize different epitopes, thus allowing to define the cross-reactivity pattern of the TCR of the present invention and other antigens (either beta-cell-derived or not) that may be further recognized. This may also be relevant to identify potential environmental triggers for type 1 diabetes, i.e. infectious or other environmental antigens that may cross-activate the T cells carrying these TCRs and thus ignite or amplify the autoimmune response against beta cells.

A further object of the present invention relates to an antibody that has specificity for a TCR of the present invention.

As used herein, the term "antibody" is used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404,097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

As used herein, the term "specificity" refers to the ability of an antibody to detectably bind the TCR of the present invention, while having relatively little detectable reactivity with other TCR. Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus non-specific binding to other irrelevant molecules. The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of antibodies is the use of Biacore instruments.

In some embodiments, the antibody of the present invention is a monoclonal antibody. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e. polypeptides of the present invention). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

In some embodiments, the antibody of the present invention is a chimeric antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies.

In some embodiments, the antibody of the present invention is a human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibodies are also "Nanobodies®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

The antibody of the present invention is suitable for therapeutic or diagnostic purposes.

In some embodiments, the antibody of the present invention is suitable for depleting the T cells that harbour the TCR of the present invention. As used herein, the term "depleting", with respect to TCR-expressing cells means a process, method, or compound that can kill, eliminate, lyse or induce such killing, elimination or lysis, so as to negatively affect the number of T cells present in a sample or in a subject that express a TCR of the present invention. In some embodiments, said depletion is mediated by antibody dependent cellular cytotoxicity (ADCC). In some embodiments, the depletion is mediated by antibody drug conjugation. Accordingly in some embodiments, the antibody of the present invention is conjugated to a cytotoxic drug. Cytotoxic drugs include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, *vinca* alkaloids, or the like.

Accordingly, a further object of the present invention relates to a method of treating type 1 diabetes in a subject in need thereof comprising administering to the subject a therapeutically effective amount of an antibody of the present invention.

In some embodiments, the antibody of the present invention is suitable for detecting a population of T cells that harbor a TCR of the present invention in a sample. Accordingly, a further object of the present invention relates to a method of detecting a population of T cells that harbor a TCR of the present invention in a sample comprising incubating the sample with an antibody of the present invention and under conditions that allow an immune complex of the TCR and the antibody to form, and detecting the presence of the immune complex.

In some embodiments, the sample is a blood sample. As used herein, the term "blood sample" refers to a whole blood sample or a sample of purified blood mononuclear cells and subsets thereof. A blood sample may be obtained by methods known in the art including venipuncture or a finger prick. Purified blood mononuclear cell samples may be obtained by density gradient centrifugation methods known in the art. The sample may be diluted with a suitable buffer before conducting the assay.

Assays and conditions for the detection of immune complexes are known to those of skill in the art. Such assays include, for example, competition assays, direct reaction assays, sandwich-type assays and immunoassays (e.g. ELISA). The assays may be quantitative or qualitative. There are a number of different conventional assays for detecting formation of an antibody-peptide complex comprising a polypeptide of the present invention. For example, the detecting step can comprise performing an ELISA assay, performing a lateral flow immunoassay, performing an agglutination assay, analysing the sample in an analytical rotor, or analysing the sample with an electrochemical, optical, or opto-electronic sensor. These different assays are well-known to those skilled in the art. In some embodiments, methods of flow cytometry are methods for detecting the T cells that harbour a TCR of the present invention. Said methods are well known in the art. For example, fluorescence activated cell sorting (FACS, BD Biosciences) may be used.

In some embodiments, the antibody of the present invention is labelled with a detectable molecule or substance, such as preferentially a fluorescent molecule, or a radioactive molecule or any other labels known in the art. Labels are known in the art that generally provide (either directly or indirectly) a signal. As used herein, the term "labelled", with regard to the antibody, is intended to encompass direct labelling of the antibody by coupling (i.e., physically linking) a detectable substance, such as a fluorophore [e.g. fluorescein isothiocyanate (FITC) or phycoerythrin (PE) or Indocyanine (Cy5)]) or a radioactive agent to the antibody, as well as indirect labelling of the probe or antibody by reactivity with a detectable substance. An antibody of the invention may be labelled with a radioactive molecule by any method known in the art. For example radioactive molecules include, but are not limited to, radioactive substances for scintigraphic studies such as I123, I124, In111, Re186, Re188.

The aforementioned assays may involve the immobilisation of the antibody of the present invention to a solid support. The solid surface could be a microtitration plate coated with the antibody. Alternatively, the solid surfaces may be beads, such as activated beads, magnetically responsive beads. Beads may be made of different materials, including but not limited to glass, plastic, polystyrene, and acrylic. In addition, the beads are preferably fluorescently labelled.

The present invention also provides chimeric antigen receptors (CARs) comprising an antigen binding domain of the antibody of the present invention. Typically, said chimeric antigen receptor comprises at least one VH and/or VL sequence of the antibody of the present invention. The chimeric antigen receptor of the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independently of antigen processing, thus bypassing a major mechanism of tumor escape. Moreover, when expressed in T-cells, CARs advantageously do not dimerize with endogenous T cell receptor (TCR) alpha and beta chains. Strategies to design and produce such CARs are well known in the art, references can be found for example in Bonini and Mondino, Eur. J. Immunol. 2015 (19), Srivastava and Riddell, Trends Immunol. 2015 (20), Jensen and Riddell, Curr. Opin. Immunol. 2015 (21), Gill and June, Immunol. Rev. 2015 (22).

In some embodiments, the invention provides CARs comprising an antigen-binding domain comprising, consisting of, or consisting essentially of, a single chain variable fragment (scFv). In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, ICOS and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

The present invention also provides a host cell comprising a nucleic acid encoding for a chimeric antigen receptor of the present invention. While the host cell can be of any cell type, can originate from any type of tissue, and can be of any developmental stage, the host cell is preferably a T cell, e.g. isolated from peripheral blood lymphocytes (PBL) or peripheral blood mononuclear cells (PBMC). In some embodiments, the T cell can be any T cell, such as a primary or in vitro expanded T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T-cell preparations can be either enriched or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell. The population of those T cells prepared as described above can be utilized in methods and compositions for adoptive immunotherapy as above described to deplete the T cells carrying a TCR of the present invention.

A further object of the present invention relates to an aptamer having specificity for a TCR of the present invention. Aptamers are a class of molecules alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. The aptamer of the present invention is also suitable for therapeutic or diagnostic purposes as above described.

A further object of the present invention relates to a primer pair comprising a first primer which is an oligonucleotide according to the present invention and a second primer which is an oligonucleotide that does not comprise a sequence of the first primer and is a fragment of the region from V to C of the TCRα or β gene in T cells, or sequences derived therefrom, wherein the first and second primers specifically bind to different strands of the TCR gene. The second primer may be complementary to a sequence of the Cβ or Cα region such that approximately 400 bp, including the V-(D)-J region of the TCRα or β gene, separate the first and second primers.

In some embodiments, the oligonucleotide of the present invention is labeled with a detectable moiety.

The primer pair of the present invention is particularly suitable for amplifying a nucleic acid sequence encoding for the TCR of the present invention. Thus, a further object of the present invention relates a method for detecting the presence of a nucleic acid sequence that encodes for the TCR of the present invention in a nucleic acid sample comprising incubating the sample with the primer pair of the present invention, amplifying the target sequence by PCR and detecting said target sequence.

The nucleic acid sample used for detecting the TCR target sequence may be a DNA sample or an RNA sample. The latter may be preliminarily converted into cDNA before proceeding with said detection. Typically, the nucleic acid sample is prepared from a blood or PBMC sample obtained from a subject. The term "PBMC" or "peripheral blood mononuclear cells" or "unfractionated PBMC", as used herein, refers to whole PBMC, i.e. to a population of white blood cells having a round nucleus, which has not been enriched for a given sub-population. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art. The template nucleic acid need not be purified. Nucleic acids may be extracted from a sample by routine techniques such as those described in Diagnostic Molecular Microbiology: Principles and Applications (Persing et al. (eds), 1993, American Society for Microbiology, Washington D.C.).

U.S. Pat. Nos. 4,683,202, 4,683,195, 4,800,159, and 4,965,188 disclose conventional PCR techniques. PCR typically employs two oligonucleotide primers that bind to a selected target nucleic acid sequence. Primers useful in the present invention include oligonucleotides capable of acting as a point of initiation of nucleic acid synthesis within the target nucleic acid sequence. A primer can be purified from a restriction digest by conventional methods, or it can be produced synthetically. If the template nucleic acid is double-stranded (e.g. DNA), it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min). If the double-stranded template nucleic acid is denatured by heat, the reaction mixture is allowed to cool to a temperature that promotes annealing of each primer to its target sequence on the target nucleic acid sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR involves use of a thermostable polymerase. The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus fiavus, T. ruber, T. thermophilus, T. aquaticus, T. lacteus, T. rubens, Bacillus stearothermophilus*, and *Methano-*

*thermus fervidus*. Nonetheless, polymerases that are not thermostable also can be employed in PCR assays provided the enzyme is replenished. Typically, the polymerase is a Taq polymerase (i.e. *Thermus aquaticus* polymerase).

The primers are combined with PCR reagents under reaction conditions that induce primer extension. Typically, chain extension reactions generally include 50 mM KCl, 10 mM Tris-HCl (pH 8.3), 15 mM MgCl2, 0.001% (w/v) gelatin, 0.5-1.0 µg denatured template DNA, 50 pmoles of each oligonucleotide primer, 2.5 U of Taq polymerase, and 10% DMSO. The reactions usually contain 150 to 320 µM each of dATP, dCTP, dTTP, dGTP, or one or more analogs thereof.

Quantitative PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase.

In order to detect and measure the amount of amplicon (i.e. amplified target nucleic acid sequence) in the sample, a measurable signal has to be generated, which is proportional to the amount of amplified product. All current detection systems use fluorescent technologies. Some of them are non-specific techniques, and consequently only allow the detection of one target at a time. Alternatively, specific detection chemistries can distinguish between non-specific amplification and target amplification. These specific techniques can be used to multiplex the assay, i.e. detecting several different targets in the same assay. For example, SYBR® Green I probes, High Resolution Melting probes, TaqMan® probes, LNA® probes and Molecular Beacon probes can be suitable. TaqMan® probes are the most widely used type of probes. They were developed by Roche (Basel, Switzerland) and ABI (Foster City, USA) from an assay that originally used a radio-labelled probe (Holland et al. 1991), which consisted of a single-stranded probe sequence that was complementary to one of the strands of the amplicon. A fluorophore is attached to the 5' end of the probe and a quencher to the 3' end. The fluorophore is excited by the machine and passes its energy, via FRET (Fluorescence Resonance Energy Transfer) to the quencher. Traditionally, the FRET pair has been conjugated to FAM as the fluorophore and TAMRA as the quencher. In a well-designed probe, FAM does not fluoresce as it passes its energy onto TAMRA. As TAMRA fluorescence is detected at a different wavelength to FAM, the background level of FAM is low. The probe binds to the amplicon during each annealing step of the PCR. When the Taq polymerase extends from the primer which is bound to the amplicon, it displaces the 5' end of the probe, which is then degraded by the 5'-3' exonuclease activity of the Taq polymerase. Cleavage continues until the remaining probe melts off the amplicon. This process releases the fluorophore and quencher into solution, spatially separating them (compared to when they were held together by the probe). This leads to an irreversible increase in fluorescence from the FAM and a decrease in the TAMRA.

The detecting method of the present invention is particularly suitable in diagnostic assays. In some embodiments, the detecting method of the present invention is particularly suitable for diagnosing type 1 diabetes in a subject, or for determining whether a subject is at risk of developing type 1 diabetes. In some embodiments, the detecting method of the present invention is particularly suitable for monitoring the treatment of a subject suffering from type 1 diabetes. For example, if after the treatment the number of cells that harbors the TCR of the present invention decreases, it may be taken as an indication that the treatment is effective for said subject.

The invention will be further illustrated by the following figures and examples. However, these examples and figures should not be interpreted in any way as limiting the scope of the present invention.

FIGURES

Figure 1A:
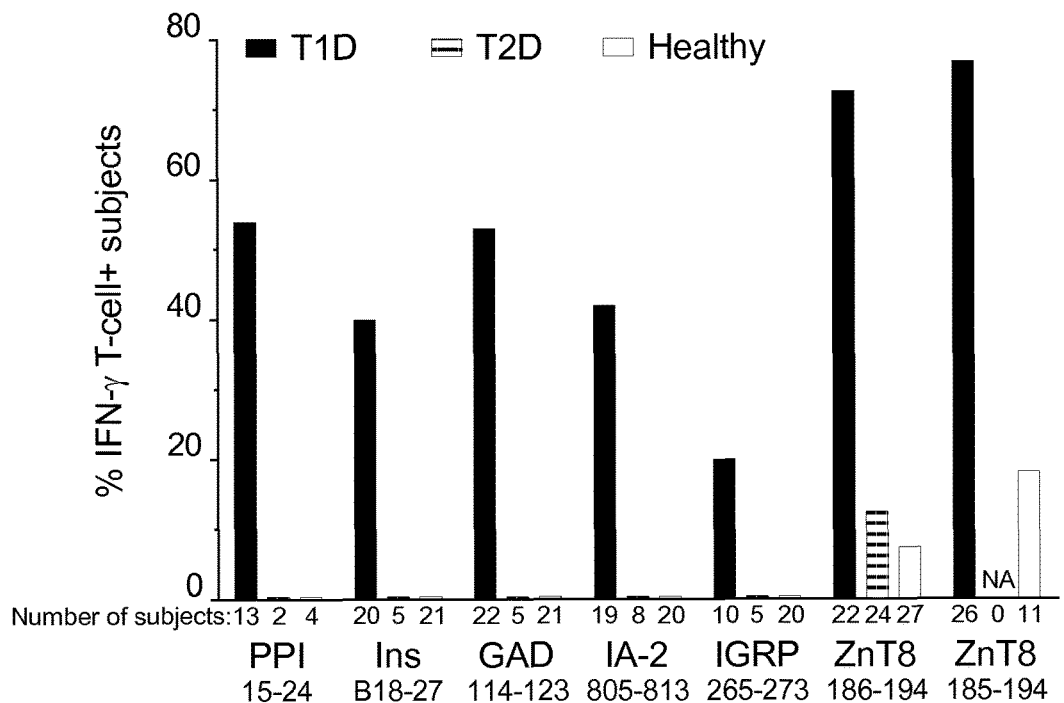
Figure 1B:
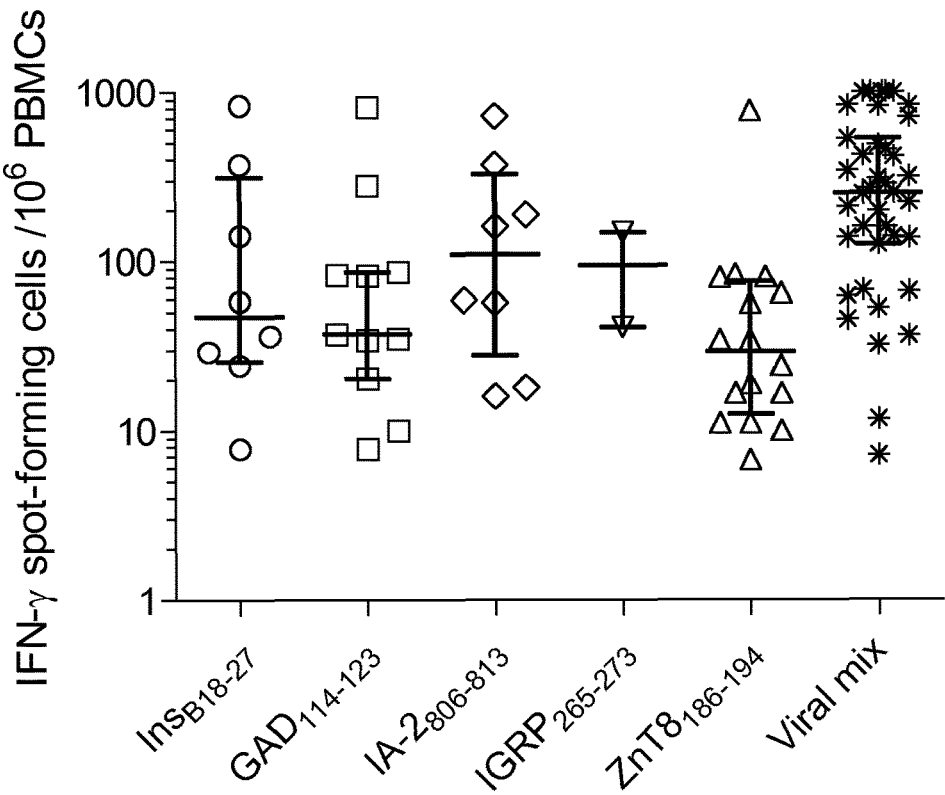

FIG. 1. Prevalence and frequency of $CD8^+$ T-cell responses against different HLA-A2-restricted n-cell epitopes. A. The prevalence of IFN-γ ELIspot responses to immunodominant epitopes derived from the major β-cell Ags preproinsulin (PPI), insulin (Ins), glutamic acid decarboxylase (GAD), insulinoma-associated Ag 2 (IA-2), islet-specific glucose-6-phosphatase catalytic subunit-related protein (IGRP) and zinc transporter 8 (ZnT8) is depicted for HLA-A2$^+$ type 1 diabetic patients (T1D; black bars), type 2 diabetic patients (T2D; hatched bars) and healthy controls (white bars). Data are from Skowera et al., J. Clin. Invest. 2008 ($PPI_{15-24}$) (2); Mallone et al., Diabetes 2007 ($Ins_{B18-27}$, $GAD_{114-123}$, $IGRP_{265-273}$) (8), Blancou et al., J. Immunol. 2007 ($IA-2_{806-813}$) (17), Scotto, Afonso et al., Diabetologia 2012 ($ZnT8_{186-194}$) (18), Enee et al., Diabetes 2012 ($ZnT8_{185-194}$) (23) and the number of subjects studied is indicated for each epitope. NA, not available. Data are from Mallone et al., Diabetes 2007 ($Ins_{B18-27}$, $GAD_{114-123}$, $IGRP_{265-273}$) (6), Blancou et al., J. Immunol. 2007 ($IA-2_{806-813}$) (15), Scotto, Afonso et al., Diabetologia 2012 ($ZnT8_{186-194}$) (16). Viral mix is a pool of Flu $MP_{58-66}$, EBV $BMLF1_{280-288}$ and CMV $pp65_{495-503}$ peptides. B. Frequencies (IFN-γ spot forming cells/$10^6$ PBMCs) of T cells reactive to each of the listed epitopes. Each symbol represents an individual patient and bars represent median±interquartile range. Data are from Mallone et al., Diabetes 2007 ($Ins_{B18-27}$, $GAD_{114-123}$, $IGRP_{265-273}$) (8), Blancou et al., J. Immunol. 2007 ($IA-2_{806-813}$) (17), Scotto, Afonso et al., Diabetologia 2012 ($ZnT8_{186-194}$) (18). Viral mix is a pool of Flu $MP_{58-66}$, EBV $BMLF1_{280-288}$ and CMV $pp65_{495-503}$ peptides.

FIG. 2. Gating strategy for the analysis of $ZnT8_{185-194}$ MMr$^+$ T cells in T1D and healthy subjects. A. Following magnetic depletion of CD8$^-$ cells in frozen-thawed PBMCs from T1D donor #11, cells were sequentially gated on small lymphocytes, singlets, live cells (Live/Dead Red), CD8$^+$ T cells (CD4/CD14/CD16/CD20/CD40$^-$CD8$^+$) and total PE$^+$, BV650$^+$, APC$^+$ and BV421$^+$ MMr$^+$ T cells. $ZnT8_{185-194}$ MMr-PE/BV421$^+$, MelanA$_{26-35}$ MMr-PE/APC$^+$ and Flu $MP_{58-66}$ MMr-APC/BV650$^+$ events were subsequently visualized using the gating strategy previously detailed for combinatorial MMr staining (24, 25) and the FlowJo v10 software. B. The final readout obtained for T1D donor #11 after gating out events positive for less or more than 2 MMr fluorochromes is shown. C. The frequency of naïve (CD45RA$^+$CCR7$^+$) cells is shown after gating on the corresponding MMr$^+$ fractions, with the distribution of total CD8$^+$ T cells shown for comparison. D-E. The final readout of MMr$^+$ cells and of naïve fractions is shown for healthy donor #20.

FIG. 3. $ZnT8_{185-194}$-specific T-cell frequency and naïve phenotype in T1D and healthy donors. A. $ZnT8_{185-194}$ MMr$^+$CD8$^+$ cells were stained ex vivo and counted as detailed in FIG. 2. Frequencies out of total CD8$^+$ T cells are depicted on the left for T1D (black circles) and healthy donors (white circles). Frequencies of MelanA$_{26-35}$ (middle)

and Flu MP$_{58-66}$ MMr$^+$CD8$^+$ cells (right) were assessed in parallel as controls. *p=0.02. B. Percent Ag-experienced (CD45RA$^-$CCR7$^-$, CD45RA$^+$CCR7$^-$ and CD45RA$^-$CCR7$^+$) cells out of total MMr$^+$ cells for each of the indicated epitopes and for total CD8$^+$ T cells. **p=0.003. C. Frequencies of naïve (CD45RA$^+$CCR7$^+$; circles) and Ag-experienced (CD45RA$^-$CCR7$^-$, CD45RA$^+$CCR7$^-$ and CD45RA$^-$CCR7$^+$; triangles) ZnT8$_{185-194}$ MMr$^+$CD8$^+$ cells in T1D (black symbols) and healthy donors (white symbols). *p=0.02. Bars in all three panels represent median values for each distribution and comparisons were performed by Mann-Whitney U test.

Figure 4:
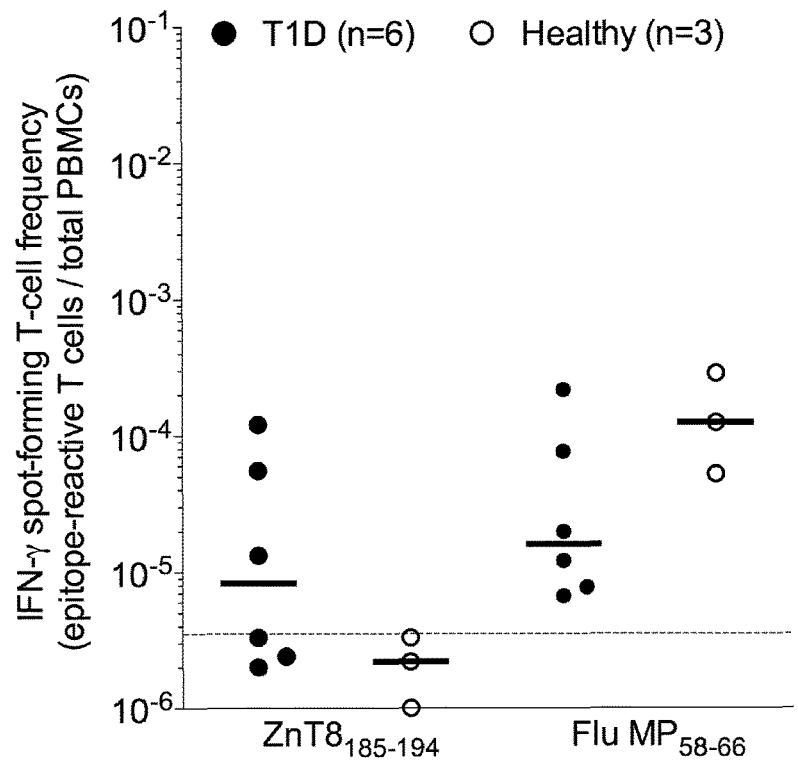

FIG. 4. ZnT8$_{185-194}$-reactive T cells detected by IFN-γ ELISpot. T1D and healthy donors previously analyzed by ex-vivo MMr staining and for whom sufficient PBMCs were available were further analyzed by IFN-γ ELISpot as previously described (18, 26). Briefly, unfractionated PBMCs (3×10$^5$/well) were plated in triplicate in ELISpot PVDF plates coated with anti-IFN-γ Abs in the presence of 10 µM ZnT8$_{185-194}$ or Flu MP$_{58-66}$ peptide or DMSO vehicle diluted in AIM-V medium supplemented with 0.5 U/ml IL-7. After 18 h, plates were revealed with biotin-conjugated anti-IFN-γ Abs (U-CyTech), alkaline phosphatase-conjugated streptavidin and NBT-BCIP substrate and counted on a BioSys Bioreader 5000 Pro-SF. Results are expressed as frequencies of epitope-reactive T cells out of total PBMCs after subtraction of background responses in the presence of DMSO alone (which were <10$^{-5}$ in all cases). The cutoff for a positive response (dotted line) was set at 3 SDs above the average background of each individual, as previously determined by receiver-operator characteristics analysis (8). A PHA polyclonal stimulus was further included as control and was positive for all samples (not shown).

FIG. 5. Isolation and functional profiling of ZnT8$_{185-194}$-specific CD8$^+$ T cells from a new-onset T1D patient. A. IFN-γ ELISpot frequencies of CD8$^+$ T cells recognizing the indicated peptides in patient D222D from day 3 up to 31 months after T1D diagnosis. ELISpot assays were performed as detailed in FIG. 4 and (18) and data is expressed as IFN-γ spot-forming cells (SFC)/10$^6$ PBMCs. The arrow indicates the time point from which clones were obtained. B. Frozen-thawed PBMCs from patient D222D collected at day 3 after diagnosis were acDC-stimulated (27) in vitro for 10 days with either ZnT8$_{186-194}$ peptide or DMSO diluent, then stained with HLA-A2 MMrs loaded with ZnT8$_{185-194}$ and labeled with either APC (Y-axis) or PE (X-axis). Gate is on viable CD8$^+$ cells. C. Double ZnT8$_{185-194}$ MMr$^+$ cells were single-cell-sorted, yielding 3 ZnT8-specific clones. A representative staining is shown for one of these D222D clones, using either cognate ZnT8$_{185-194}$ MMrs or control Melan-A$_{26-35}$ MMrs. D. D222D clone 1 was stimulated for 6 h with K562-A2 cells pulsed with the indicated peptides at different concentrations. Percent of intracellular TNF-α$^+$ cells is shown for each dot plot, gated on viable CD8$^+$ cells. E. Recall assays were performed on D222D clones as above and the percent of TNF-α$^+$, IFN-γ$^+$, IL-2$^+$ and MIP-1β$^+$ cells were calculated as in (D). Results refer to a representative of three experiments performed.

FIG. 6. Cytotoxicity of ZnT8$_{185-194}$-specific CD8$^+$ T cells from patient D222D. A. HLA-A2$^+$ LCL target cells were labeled with FarRed, pulsed with either ZnT8$_{185-194}$ (top) or control Flu MP$_{58-66}$ peptide (bottom) and cultured for 24 h with CFSE-labeled D222D clone 3 at increasing effector/target ratios (E/T; left to right). Live FarRed$^+$ target cells were counted at the end of the culture and normalized to a fixed amount of beads added to each well. Percent lysis is noted for each dot plot, calculated as 100×(live targets cultured alone)−(live targets in the presence of T cells)/(live targets cultured alone). B. Lysis of LCL targets pulsed with the indicated peptides and cultured with D222D clones at different E/T ratios. Percent lysis was calculated as above and depicted as mean±SEM of two independent experiments with clone 2 and 3, with data depicted in panel (A) used for clone 3. Similar profiles were obtained for clone 1 (not shown). C. ZnT8-specific lysis of peptide-pulsed LCL target cells co-cultured for 4 h with D222D clone 2 without inhibitors (−) or in the presence of concanamycin A (CMA, 100 nM), brefeldin A (BFA, 5 µg/ml), anti-FasL mAb (aFasL, clone NOK-1; 5 µg/ml) or IgG1 isotype control. *p<0.05 by Wilcoxon signed-rank test. Results are mean±SEM of triplicate measurements from one representative experiment out two performed.

FIG. 7. Overview of the ZnT8$_{185-194}$-reactive CD8$^+$ T-cell clones generated. A. Summary of clones isolated from T1D and healthy subjects. Clones in parentheses could not be stabilized in long-term cultures and underwent more limited characterization. B. Staining of the indicated clones with HLA-A2 MMrs loaded with ZnT8$_{185-194}$ (top row) its shorter ZnT8$_{186-194}$ variant (middle row) or control MelanA$_{26-35}$ peptide (bottom row). Gate is on viable CD8$^+$ cells.

FIG. 8. ZnT8$_{185-194}$-specific CD8$^+$ T cells isolated from healthy subjects display lower Ag avidity and polyfunctionality. A. PBMCs from healthy donor H314C were stained ex vivo with ZnT8$_{185-194}$-loaded HLA-A2 MMrs labeled with either PE (Y-axis) or BV421 (X-axis). Gate is on viable CD8$^+$ cells. B. CD45RA and CCR7 staining of double ZnT8$_{185-194}$ MMr$^+$CD8$^+$ cells. C. ZnT8$_{185-194}$ MMr staining of the clone obtained, gated on viable cells. D. ZnT8$_{185-194}$ HLA-A2 MMr staining of the indicated T-cell clones in the absence (−) or presence (+) of dasatinib. E. Median fluorescence intensity (MFI) of ZnT8$_{185-194}$ MMr staining for the indicated clones in the absence (white bars) or presence (black bars) of dasatinib. MFI is normalized to that of D222D clone 2 in the presence of dasatinib. Data for single clones are mean±SEM of two experiments and cumulative results for T1D and healthy clones are shown in the last two bar groups. *p=0.05. F-G-H. D222D clone 2 (F), H017N clone A1 (G) and H314C clone 6C4 (H) were stimulated for 6 h with K562-A2 cells pulsed with ZnT8$_{185-194}$ peptide over a 0.01-100 µM concentration range and percent of TNF-α$^+$, IFN-γ$^+$, IL-2$^+$, and MIP-1β$^+$ cells out of viable CD8$^+$ cells calculated. Representative experiments are shown out of three performed. I. Half maximal effective peptide concentration (EC50; left Y-axis—white and black symbols on the left for T1D and healthy clones, respectively) and maximal response (i.e. percent of cytokine-positive T cells at optimal peptide concentrations; right Y-axis—white and black symbols on the right for T1D and healthy clones, respectively) for the indicated clones and cytokine responses. Clones were stimulated as above and data in panels F-G-H was used for clones D222D 2, H017N A1 and H314C 6C4, respectively. Bars display median values for each distribution and results are representative of 2 to 4 separate experiments. *p=0.05. J. Polyfunctionality distribution of T1D (left) and healthy clones (right). Percent T cells producing 0 to 4 cytokines among TNF-α, IFN-γ, IL-2 and MIP-1β upon exposure to K562-A2 cells pulsed with 100 µM ZnT8$_{185-194}$ peptide are shown. The polyfunctionality index is shown and was calculated as described (28); p=0.02 by ANOVA.

FIG. 9. Target cell lysis by ZnT8$_{185-194}$-reactive CD8$^+$ T cells from T1D and healthy donors. (A-C) Lysis of K562-A2 cells transfected (A) or not (B) with a ZnT8 plasmid and cultured for 24 h with clones D222D 2, H017N A1 or H314C 6C4. Panel C shows K562-A2/ZnT8 targets pulsed with 10 μM ZnT8$_{185-194}$ peptide. Percent lysis was calculated as in FIG. 6. Results are shown as mean±SEM of triplicate wells from two separate experiments. *p=0.029. (D-E) xCEL-Lingence real-time cytotoxicity of D222D clone 2 (D) and control H004N MelanA$_{26-35}$-reactive clone M2 (E) on the HLA-A2$^+$ ECN90 (open triangles) or control HLA-A2$^-$ EndoC-βH2 β-cell line (open circles) at 2:1 E/T ratio. Black symbols show the corresponding targets pulsed with 10 μM ZnT8$_{185-194}$ (D) or MelanA$_{26-35}$ peptide (E). Mean±SEM of triplicate measurements are shown at each indicated time point, where t=0 is the time when T-cell effectors were added and to which all values were normalized. Representative experiments out of at least two performed are shown for each panel.

FIG. 10. Modulation of HLA Class I expression on human β-cell lines. A-B. Surface HLA Class I expression and viability of HLA-A2$^+$ ECN90 (A) and HLA-A2$^-$ EndoC-βH2 cell lines (B) in basal condition and upon exposure to the indicated cytokines for 18 h. The following cytokine cocktails were used following published protocols (2, 29) and further optimization: TNF-α alone (1,100 U/ml); IFN-α alone (500 U/ml); IFN-γ alone (500 U/ml); TNF-α, IFN-γ and IL-1β (1,100 U/ml, 2,000 U/ml and 1,000 U/ml, respectively); TNF-α, IFN-α, IFN-γ and IL-1β (2,500 U/ml, 1,000 U/ml, 500 U/ml and 50 U/ml, respectively). A representative experiment out of three performed is depicted. C-D. Representative optical microscopy images (10× magnification) of wells in which ZnT8-specific D222D clones (C) or MelanA-specific clones (D) were co-cultured with HLA-A2$^+$ ECN90 or HLA-A2$^-$ EndoC-βH2 cells for the cytotoxicity assays depicted in FIG. 9D-E. T cells were removed by gentle washing and remaining cells stained with Trypan Blue. Two independent experiments were performed.

FIG. 11. TCR sequences of ZnT8$_{185-194}$-specific CD8$^+$ T-cell clones from T1D subjects. TCR β and α chain amino acid and nucleotide sequences of ZnT8$_{185-194}$-specific CD8$^+$ T-cell clones from T1D donors are shown. Rearranged nucleotide sequences are presented as V segments (underlined) followed by (ND)N segments (not underlined; N additions denoted in bold) and then by J segments (underlined), as annotated using the IMGT database (www.imgt.org).

FIG. 12. TCR sequences of ZnT8$_{185-194}$-specific CD8$^+$ T-cell clones from healthy subjects. A-B. TCR β and α chain amino acid and nucleotide sequences of ZnT8$_{185-194}$-specific CD8$^+$ T-cell clones from healthy donors are shown. Rearranged nucleotide sequences are presented as for FIG. 11.

Figure 13:
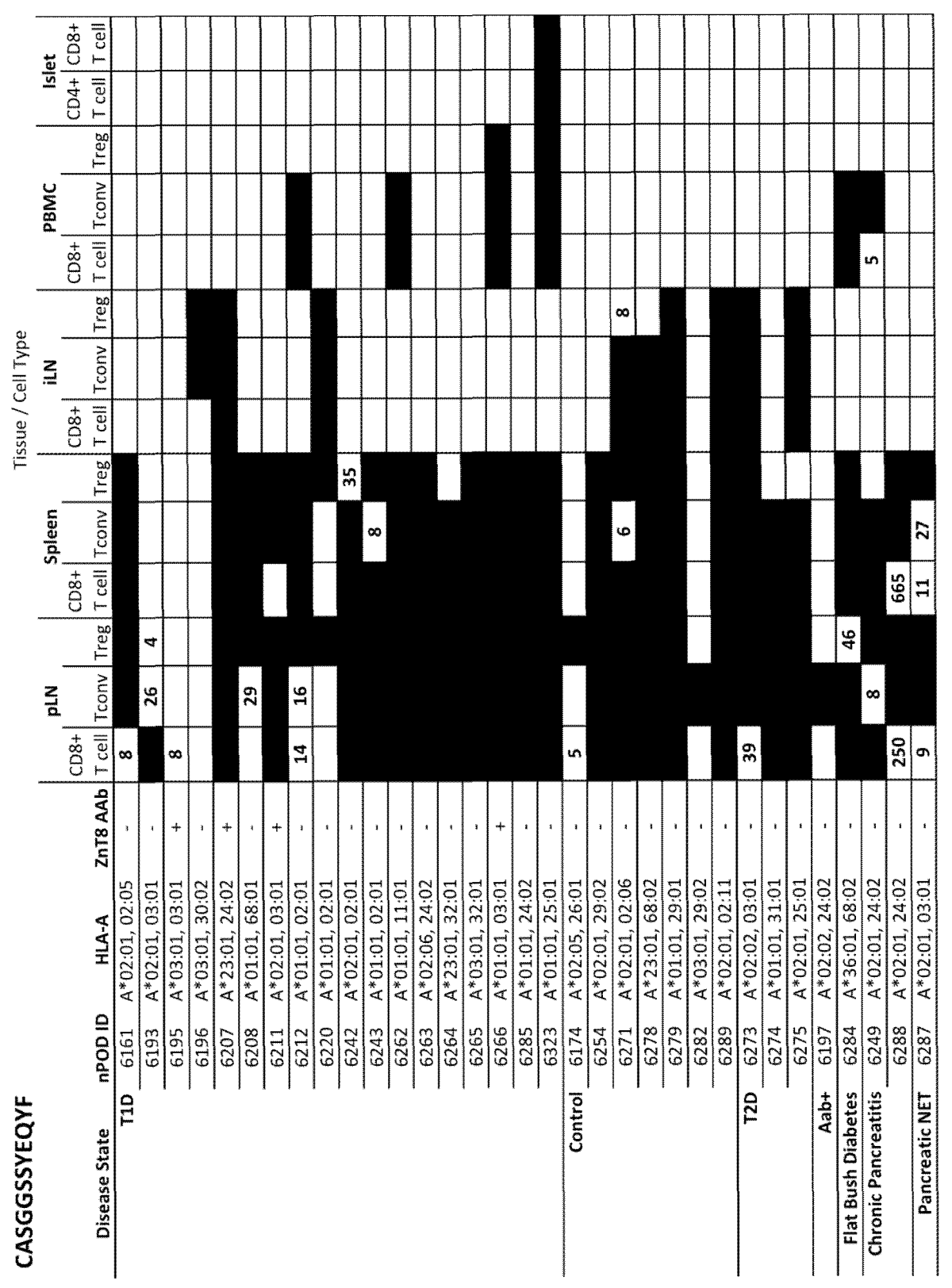

FIG. 13. Detection of the D010R TCRβ sequence in nPOD samples. In silico search for the D010R TCRβ aminoacid sequence in the polyclonal T-cell repertoire of CD8$^+$ T cells, conventional CD4$^+$ (Tconv; CD127$^+$) and regulatory CD4$^+$ (Treg; CD25$^+$CD127$^-$) obtained from tissues [including pancreatic (pLN) and inguinal lymph nodes (iLN)] of the indicated nPOD cases. Black and white cells indicate samples that were sequenced or not, respectively. Samples positive for the D010R TCRβ aminoacid sequence are marked in white with numbers indicating its frequency per 10$^6$ TCRs. Data was obtained by interrogating the publicly available nPOD TCR/BCR search database (http://clonesearch.jdrfnpod.org) compiled from source data generated in the Brusko Laboratory (University of Florida).

EXAMPLE

Material & Methods

Peptides, HLA-A2 Binding Measurements and HLA-A2 MMr Synthesis.

Peptides ZnT8$_{185-194}$ (AVAANIVLTV; SEQ ID NO: 49), ZnT8$_{186-194}$ (VAANIVLTV; SEQ ID NO: 50), Melan-A$_{26-35}$ (A27L variant; ELAGIGILTV; SEQ ID NO: 51) and Flu MP$_{58-66}$ (GILGFVFTL; SEQ ID NO: 52) were synthesized by ChinaPeptides at >85% purity. HLA-A2 MMrs were produced with the one-pot, mix-and-read technology (30) and staining performed in the presence of 50 nM dasatinib (31).

Ex-Vivo Analysis of ZnT8$_{185-194}$-Specific CD8$^+$ T Cells.

Frozen-thawed PBMCs (~4×10$^6$ after thawing) from recent-onset T1D patients (n=12; median age 12 years, range 8-18; 25% females; T1D duration 14 months, 5-24) and age- and sex-matched healthy controls (n=14; median 12-year-old, 9-40; 36% females) were magnetically enriched for CD8$^+$ T cells by negative selection (Stemcell Technologies) and stained with Live/Dead Red (Life Technologies), CD4/CD14/CD16/CD20/CD40-FITC, CD8-AlexaFluor700, CD45RA-Brilliant Violet (BV)785 (all from eBioscience), CCR7-BV711 (clone 150503; BD), ZnT8$_{185-194}$ MMr-PE/BV421, MelanA$_{26-35}$ MMr-PE/APC and Flu MP$_{58-66}$ MMr-APC/BV650, using a combinatorial MMr staining approach (24) detailed in FIG. 2. A mean of 3.8×10$^5$ and a minimum of 1.2×10$^5$ CD8$^+$ T cells were acquired on a 15-color FACSAria III cytometer. IFN-γ ELISpot assays were performed as previously (18).

Cloning of ZnT8$_{185-194}$-Specific T Cells.

D222D CD8$^+$ T-cell clones were obtained from a new-onset T1D male patient (60-year-old; BMI 22 kg/m$^2$; anti-GAD$^+$, anti-IA-2$^-$, anti-ZnT8$^+$) blood-drawn 3 days after T1D onset presenting with ketoacidosis and an HbA1c of 13.5%. D010R clones were from a 12-year-old boy diagnosed with ketoacidosis and T1D (HbA1c 12.7%; anti-GAD$^-$, anti-IA-2$^+$; BMI 16 kg/m$^2$) 8 days before drawing. Briefly, 2-10×10$^6$ frozen-thawed PBMCs were plated at 10$^7$ cells/ml in AIM-V medium (Life Technologies) supplemented as described for our acDC protocol (27) in the presence or absence of 1 μM ZnT8$_{186-194}$ or ZnT8$_{185-194}$ peptide. On day 2, 5% T-cell growth factor (Hemagen) and 0.1 ng/ml IL-15 (R&D) were added and the culture further left undisturbed until day 10, at which time single-cell sorting of ZnT8$_{185-194}$ MMr-PE/APC$^+$CD8$^+$ cells was performed in 96-well U-bottom plates. For donor H314C, ZnT8$_{185-194}$ MMr-PE/BV421$^+$CD8$^+$ cells were sorted directly ex vivo from 10$^7$ frozen-thawed PBMCs. Each sorting well contained 200,000 irradiated PBMCs from 3 different donors, 5% Cellkines (Zeptometrix), 200 IU/ml IL-2 (Proleukin), 25 ng/ml IL-15, 1 μg/ml PHA-L (Sigma), penicillin/streptomycin and amphotericin B. The same medium without PHA was replenished every 3 days and growing clones selected by visual inspection and transferred into 48-well plates for specificity testing. Clones thus obtained (FIG. 7A) were restimulated every 2-3 weeks with fresh feeders in the same medium in 25-cm$^2$ flasks.

Antigen Recall Assays.

Ag-presenting cells were labeled with CellTrace Violet (Life Technologies) to separate them from T cells and incubated at 2:1 T:Ag-presenting cell ratio for 6 h with the indicated peptide-pulsed APCs (K562-A2 cells, transduced with HLA-A*02:01, CD80 and 4-1BBL, a kind gift of Dr. J. Riley, University of Pennsylvania, Philadelphia, Pa.; or HLA-A2$^+$ LCL cells) in the presence of 10 μg/ml brefeldin A. Intracellular cytokine staining was performed using BD Cytofix/Cytoperm reagents and analyzed on a 16-color BD LSR Fortessa cytometer.

Cytotoxicity Assays.

LCL pulsed with 10 μM of the indicated peptide, K562-A2/ZnT8 or K562/A2 target cells were labeled with Cell-Trace FarRed (Life Technologies) and dispensed in 96-well flat-bottom plates at $10^5$/well. Different numbers of CFSE-labeled T cells were added and co-cultured for 6-24 h, as indicated. Following staining with Live/Dead Aqua (Life Technologies) and fixation, a fixed number of CompBeads (BD) was added to each well. Flow cytometry analysis was performed by counting numbers of $CFSE^-FarRed^+Live/Dead^-$ targets in each condition, normalized to equal numbers of CompBeads. To explore cytotoxic mechanisms, concamycin A (100 nM), brefeldin A (5 μg/ml) or blocking anti-FasL mAb (clone NOK-1, 5 μg/ml) were used.

The EndoC-βH2 cell line (HLA-A*01/03, -B*07/08, -C*07/07) has been previously described (32). The ECN90 cell line (HLA-A*02:01/03, -B*40/49, -C*03/07) was derived from a human neonatal pancreas using previous protocols (32). Real-time cytotoxicity assays on β-cell lines were performed with the xCELLigence system (ACEA Biosciences). Briefly, β cells were pre-treated as indicated and plated on 96-well E-plates. After resting for 20 h and pulsing with 10 μM of the indicated peptides or DMSO diluent alone for an additional 2 h, T cells were added at 2:1 E/T ratio and impedance recorded every 5 min for 2 h, then every 15 min for an additional 2 h. Cell indexes were normalized to values at the time of T-cell addition and transformed into percent lysis values as above.

TCR Sequencing.

TCR sequencing was performed as detailed (33, 34) with minimal modifications. In brief, unbiased amplification of all expressed TRB and TRA gene products was conducted using a template-switch anchored RT-PCR with chain-specific constant region primers. Amplicons were sub-cloned, sampled, sequenced and analyzed. The IMGT nomenclature is used in this report (35).

Statistics.

Values are expressed as median (range). Comparisons of means between two groups were performed with two-sided Wilcoxon signed-ranks test and Mann-Whitney U test for paired and unpaired samples, respectively.

Study Approval.

All study subjects provided written informed consent. The study was approved by the Comité de Protection des Personnes Ile de France 1-2 (AOR10049, K091101, A01094-53).

Results $ZnT8_{185-194}$-specific $CD8^+$ T cells are found at similar frequencies in T1D and healthy children but display an Ag-experienced vs. naïve phenotype.

We previously reported that, when compared to HLA-A2-restricted responses towards other β-cell epitopes (2, 8, 17), $ZnT8_{186-194}$-reactive IFN-γ-secreting $CD8^+$ T-cell responses are higher in prevalence (FIG. 1A) but similar in frequency (FIG. 1B) among $HLA-A2^+$ new-onset T1D patients (18). Curiously, they are less T1D-specific, as they were also detected in some (7-18%) type 2 diabetic (T2D) and healthy individuals. We therefore set forth to analyze the corresponding T cells independently of their functional phenotype, using HLA-A2 multimers (MMrs).

Figure 3A:
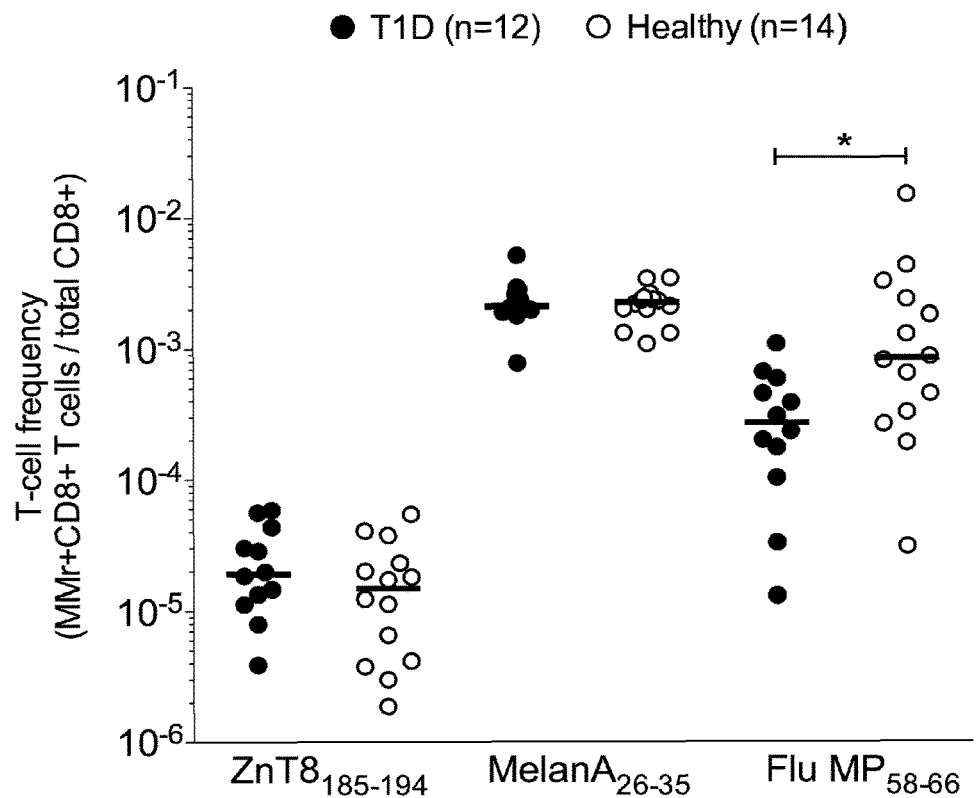
Figure 3B:
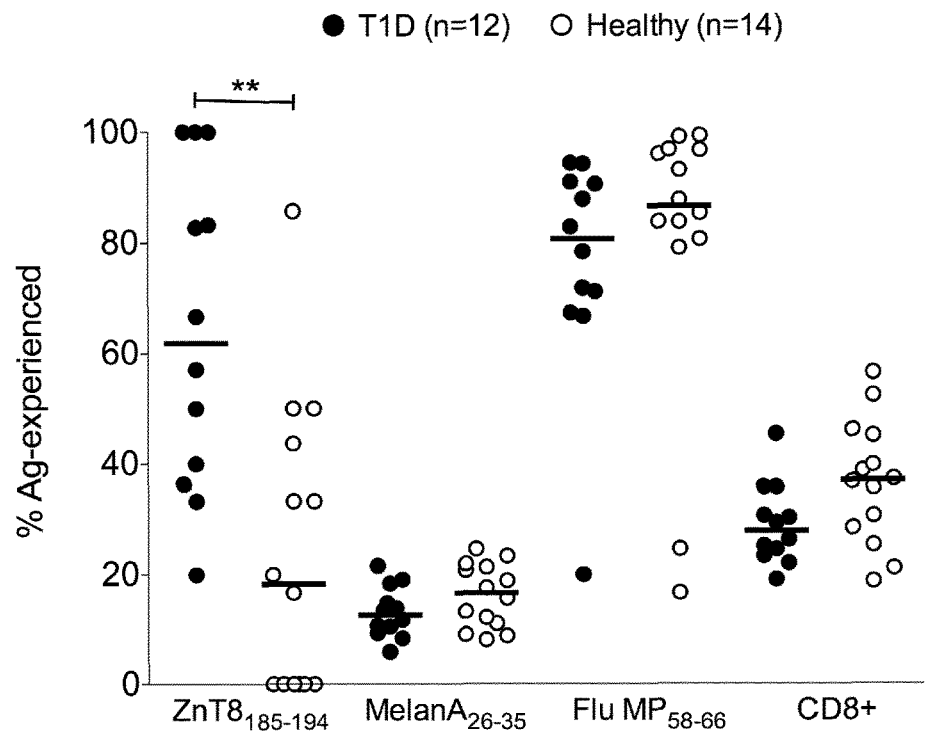
Figure 3C:
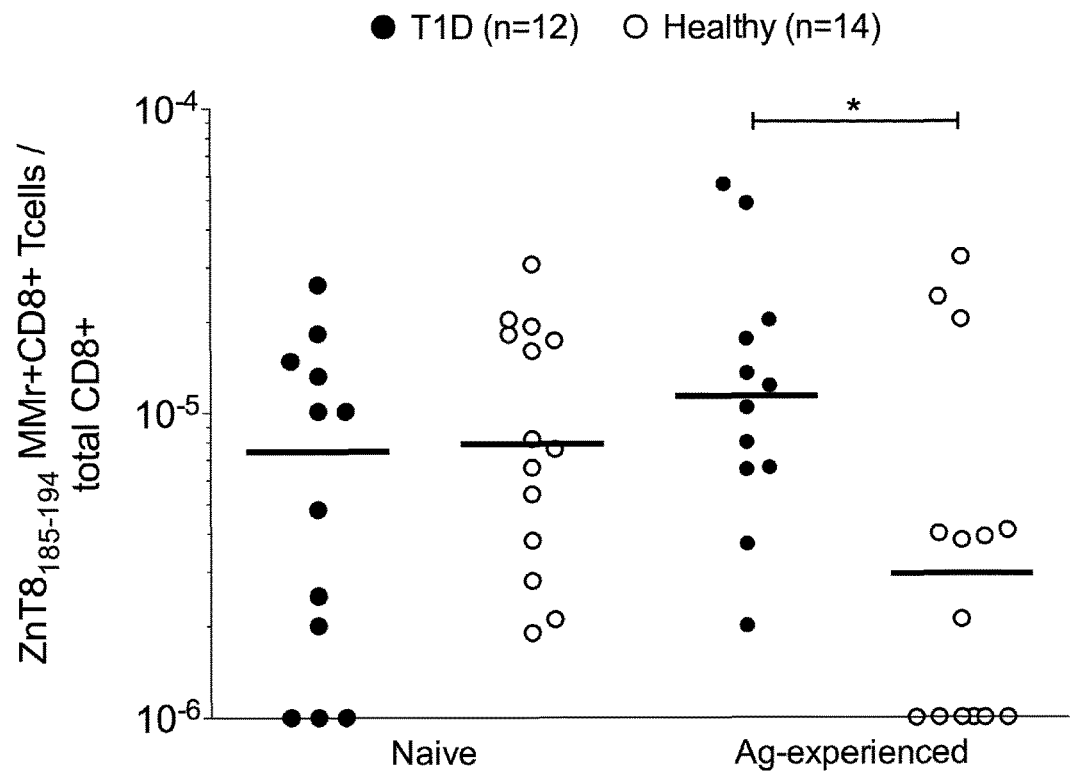

To synthesize the reagents, we compared the $ZnT8_{186-194}$ epitope with a longer $ZnT8_{185-194}$ variant for which a similar immunodominance was reported (23), possibly arising from the same T cells. Affinity and stability measurements of recombinant HLA-A2 molecules complexed with these two variants indicated that $ZnT8_{185-194}$ (AVAANIVLTV; SEQ ID NO: 49) exhibited lower affinity ($K_D$=207 nM vs. 15 nM) but higher stability ($t_{1/2}$ 2.3 h vs. 1.8 h) than the shorter $ZnT8_{186-194}$ epitope (VAANIVLTV; data not shown). We privileged the stability parameter (36), hence choosing $ZnT8_{185-194}$ for loading onto HLA-A2 MMrs. MMrs were labeled with two different fluorochromes to increase staining specificity (24) at detecting ZnT8-reactive $CD8^+$ T cells directly ex vivo in 12 $HLA-A2^+$ recent-onset T1D and 14 age- and sex-matched healthy children. A representative staining is presented in FIG. 2 along with the gating strategy used. As shown in FIG. 3A, there was no significant difference in the frequency of $ZnT8_{185-194}$ $MMr^+CD8^+$ T cells in T1D and healthy children (median $2\times10^{-5}$ $CD8^+$ T cells, range $4\times10^{-6}$- $6\times10^{-5}$ vs. $1\times10^{-5}$ $CD8^+$ T cells, $2\times10^{-6}$-$5\times10^{-5}$). This was true also for control $MelanA_{26-35}$ $MMr^+$ $CD8^+$ T cells, which displayed ~100-fold higher frequencies (median $2\times10^{-3}$ $CD8^+$ T cells); while Flu $MP_{58-66}$ $MMr^+$ $CD8^+$ T cells, which were 10-15-fold more abundant than $ZnT8_{185-194}$ $MMr^+$ ones, were slightly more represented in healthy than in T1D children ($8\times10^{-4}$ vs. $3\times10^{-4}$; p=0.02). However, $ZnT8_{185-194}$ $MMr^+CD8^+$ T cells mostly displayed an Ag-experienced ($CD45RA^-CCR7^-$, $CD45RA^+CCR7^-$ and $CD45RA^-CCR7^+$) phenotype in T1D but not in healthy children (FIG. 3B; median 62%, range 20-100% vs. 18%, 0-86%; p=0.003). This phenotype difference did not reflect higher frequencies of $ZnT8_{185-194}$ $MMr^+CD8^+$ naïve T cells in healthy children, but rather higher frequencies of Ag-experienced T cells in T1D children (FIG. 3C; p=0.02). The MelanA and Flu $MMr^+CD8^+$ control T cells displayed the expected naïve and Ag-experienced phenotype, respectively, without differences between T1D and control children (FIG. 3B; median 13-17% and 81-87% Ag-experienced $MMr^+$ $CD8^+$ T cells). This Ag-experienced phenotype was mostly composed of effector memory ($CD45RA^-CCR7^-$) cells, both for ZnT8 and Flu $MMr^+CD8^+$ T cells (FIG. 2C-E). There was no difference in $ZnT8_{185-194}$ MMr fluorescence intensity between T1D and control children (data not shown), but such difference, if present, may be masked by dasatinib pre-treatment, a protein kinase inhibitor which stabilizes MMr interactions with T-cell receptors (TCRs), particularly with low-affinity ones (31). Despite detection of these $CD8^+$ T cells at similar frequencies in both T1D and healthy children by MMrs, analysis of some samples for which sufficient cells were available by IFN-γ ELISpot replicated the higher prevalence of these responses associated with T1D status (FIG. 4), as previously observed (18).

Collectively, these results show that $ZnT8_{185-194}$-specific $CD8^+$ T cells are similar in frequency but differentially Ag-experienced between T1D and healthy children.

$ZnT8_{185-194}$-Specific $CD8^+$ T Cells Isolated from a New-Onset T1D Patient Display Strong Ag Avidity and Cytotoxicity.

Figure 5A:
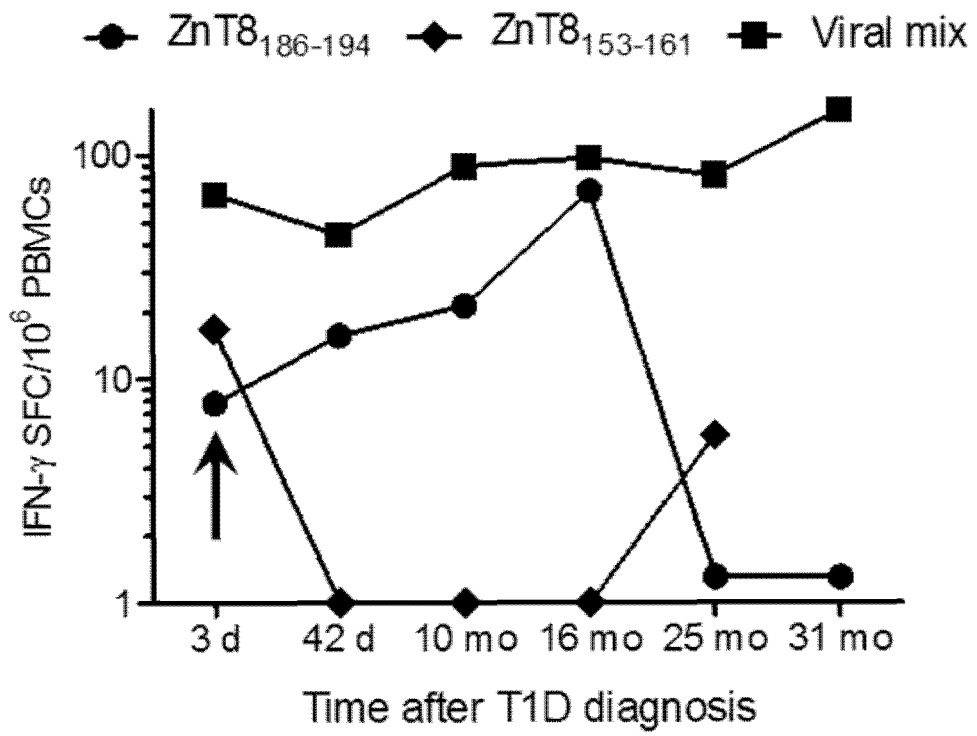
Figure 5B:
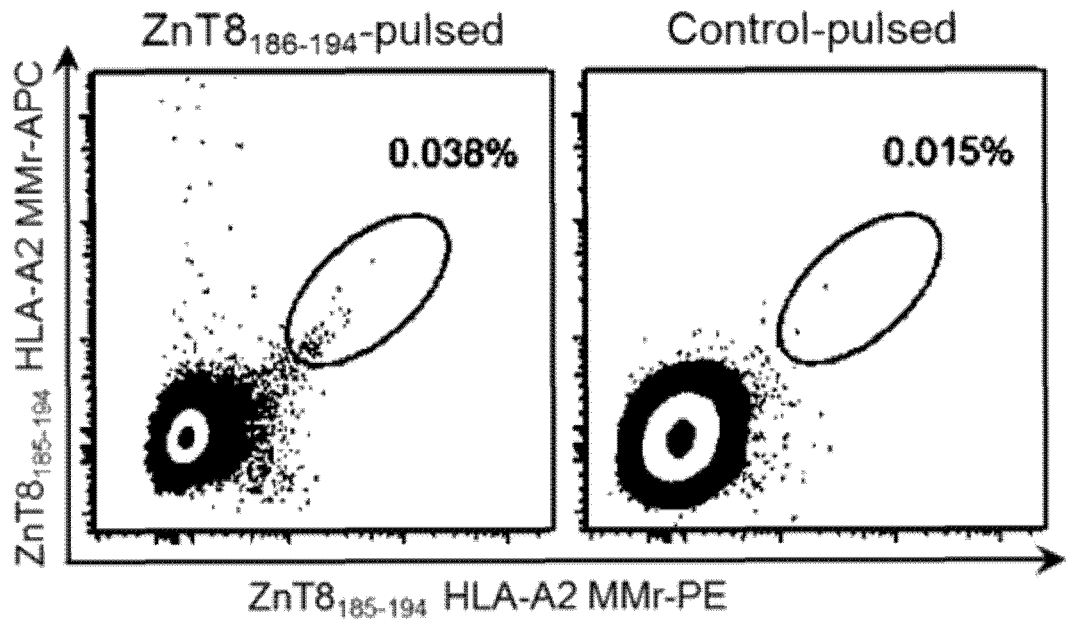
Figure 5C:
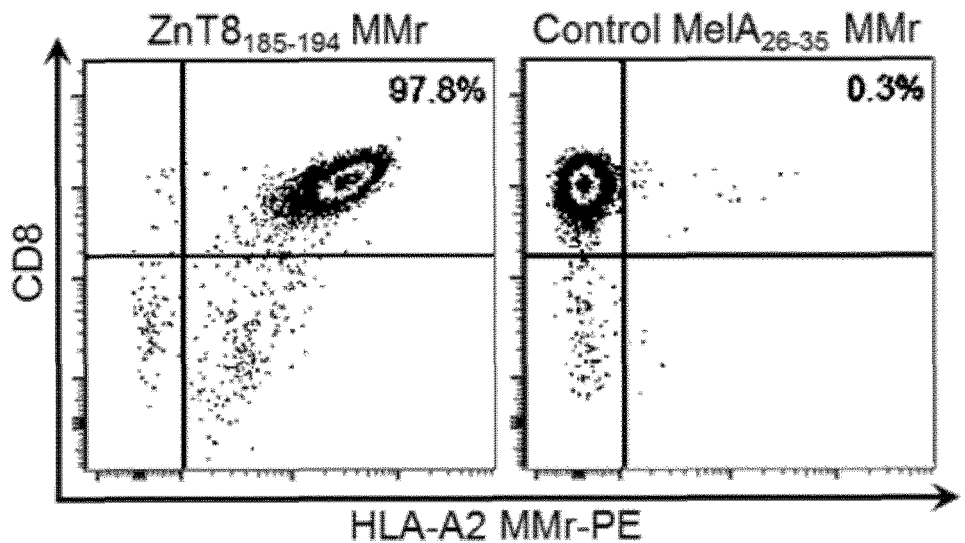

Prior in vivo Ag priming may result in selection of $ZnT8_{185-194}$-specific $CD8^+$ T cells with high Ag avidity, but the high end of this avidity range is normally pruned by thymic selection in the case of autoreactive T cells (37). To test this possibility, we isolated ZnT8-reactive $CD8^+$ T cells from a new-onset T1D patient (#D222D) displaying high ELISpot frequencies of $ZnT8_{186-194}$-reactive IFN-γ-producing $CD8^+$ T cells (18) up to 16 months after diagnosis (FIG. 5A; 7.8-68.9 spot-forming cells/$10^6$ PBMCs, i.e. 0.0008-0.007%). PBMCs were stimulated in vitro with or without the shorter $ZnT8_{186-194}$ peptide variant originally used. We employed our accelerated co-cultured dendritic cell (acDC) technology (27) to expand this minute Ag-specific fraction from the limited number of unfractionated frozen-thawed PBMCs available ($2\times10^6$). After 10 days, staining with double-labeled $ZnT8_{185-194}$-loaded HLA-A2 MMrs revealed 0.038% double-MMr+ cells out of the total CD8+ fraction compared to 0.015% in control cultures (FIG. 5B). These cells were single-cell sorted (n=100) and cloned, yielding 5 (5%) growing wells, 3 of which stained uniformly positive with $ZnT8_{185-194}$ MMrs (FIG. 5C). Since these T cells were stimulated with the $ZnT8_{186-194}$ peptide and sorted using $ZnT8_{185-194}$-loaded MMrs, both epitope variants are recognized by the same T cells, as confirmed by in vitro recall assays (data not shown).

Figure 5D:
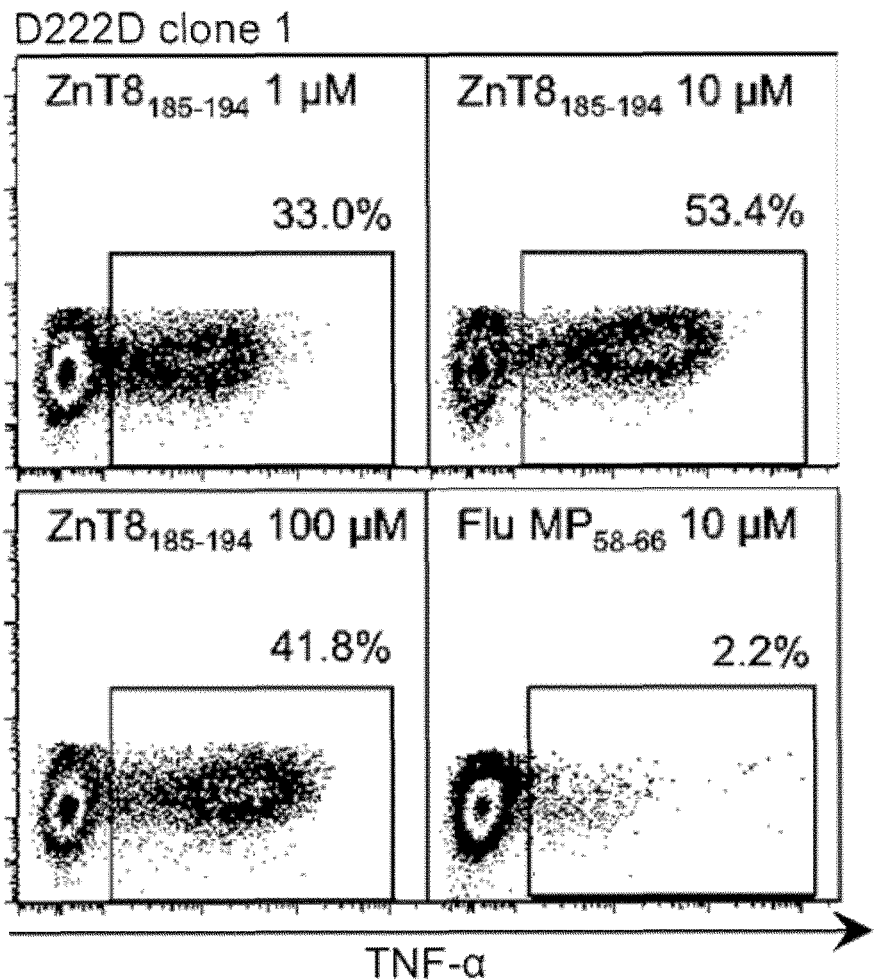
Figure 5E:
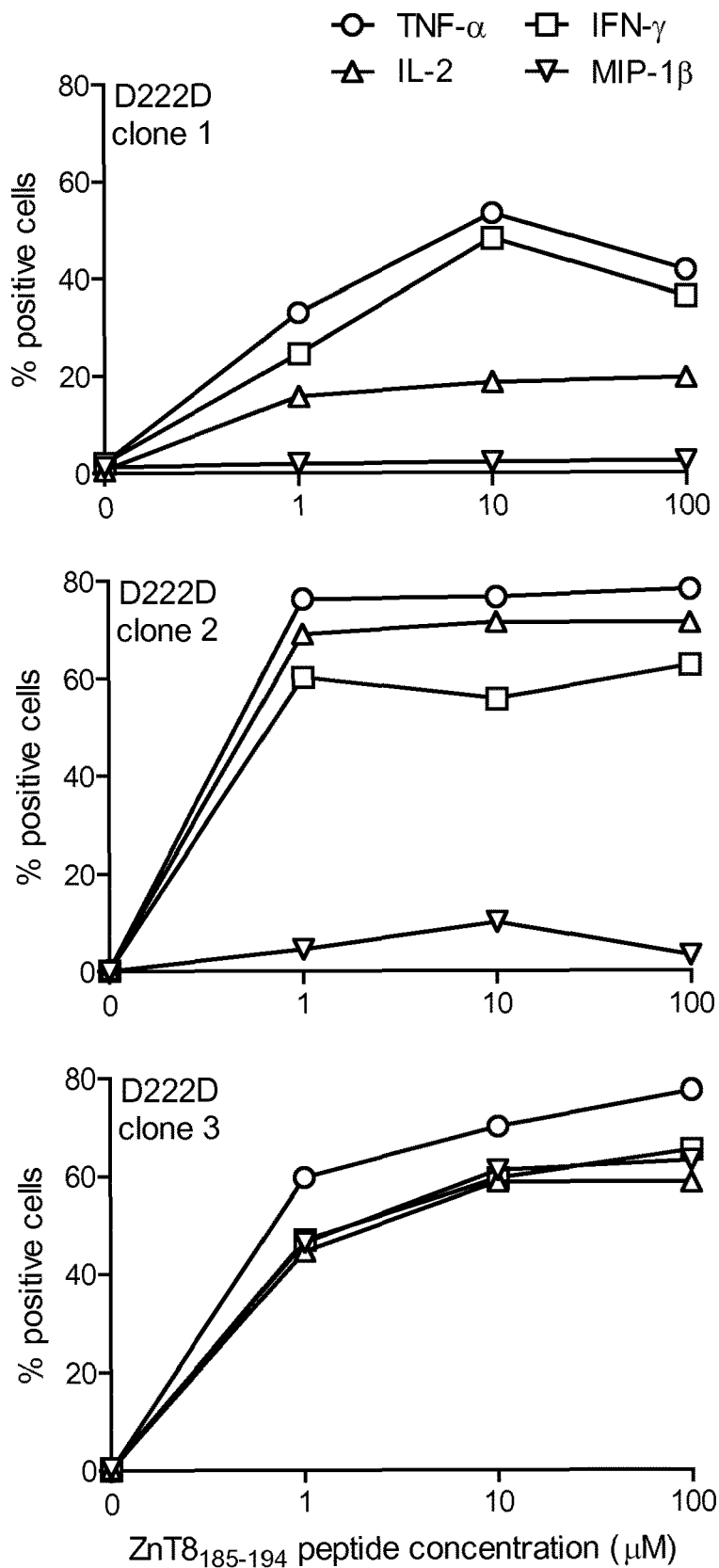

These D222D CD8+ T-cell clones responded to $ZnT8_{185-194}$-pulsed HLA-A2-transduced K562 (K562-A2) cells in in vitro recall assays. A representative intracellular TNF-α staining is shown in FIG. 5D for D222D clone 1, and results for all 3 clones are summarized in FIG. 5E. The response was dose-dependent up to 1-10 μM peptide concentrations, with concomitant production of TNF-α, IFN-γ and IL-2. Clone 3 and, to a lesser extent, clone 2 also produced MIP-1β.

Figure 6A:
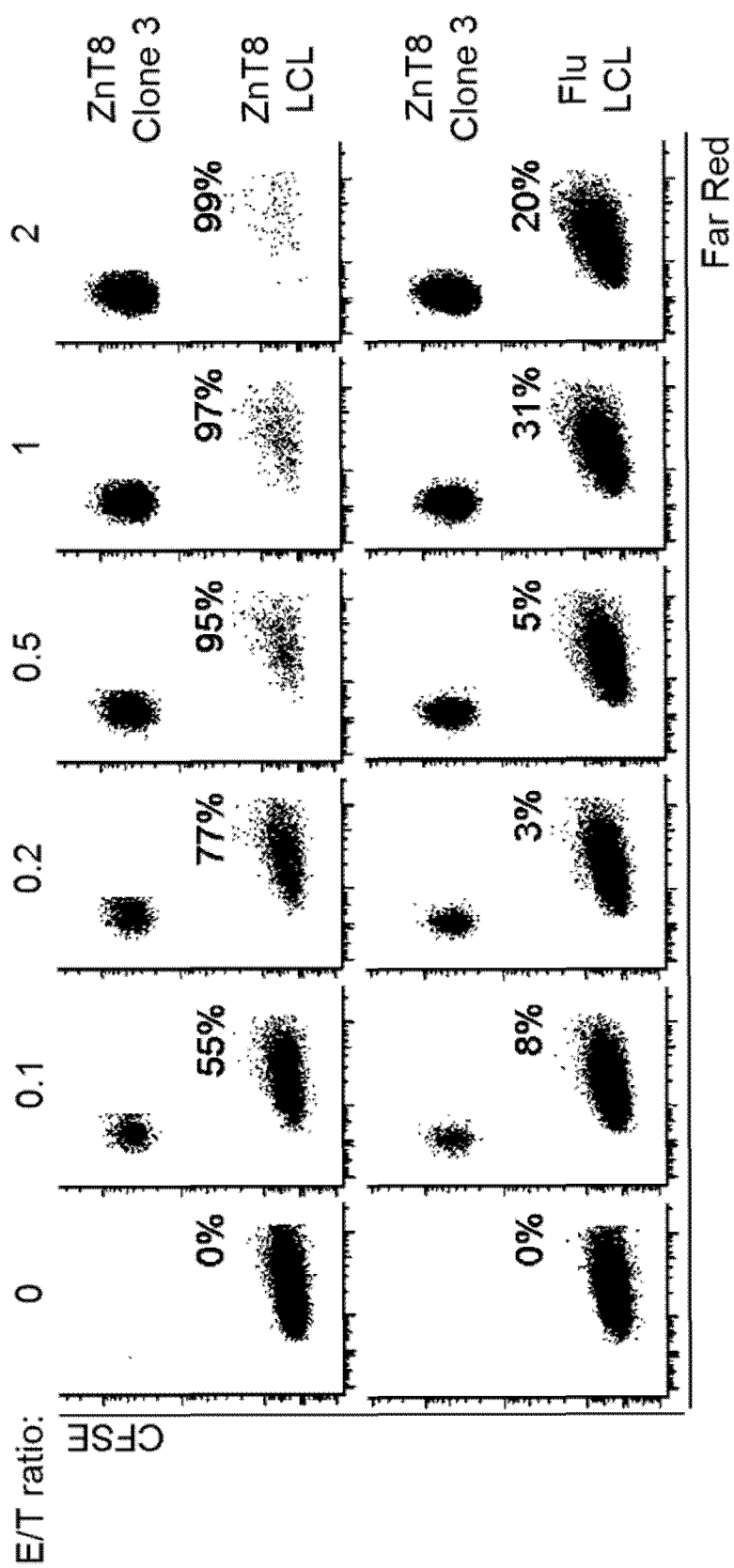
Figure 6B:
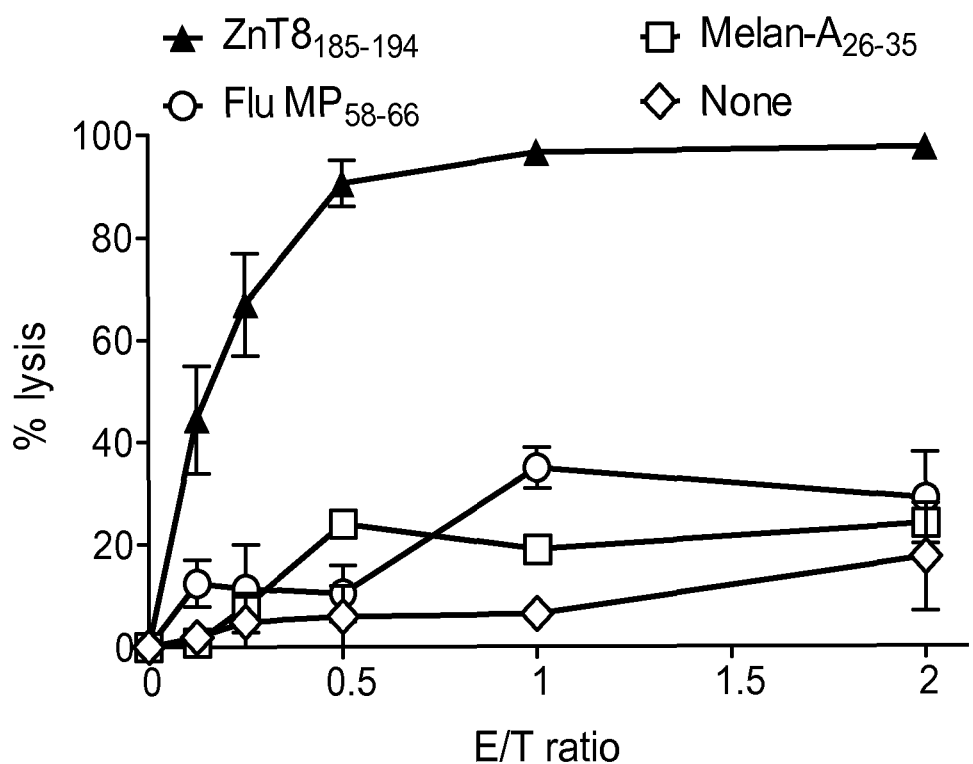
Figure 6C:
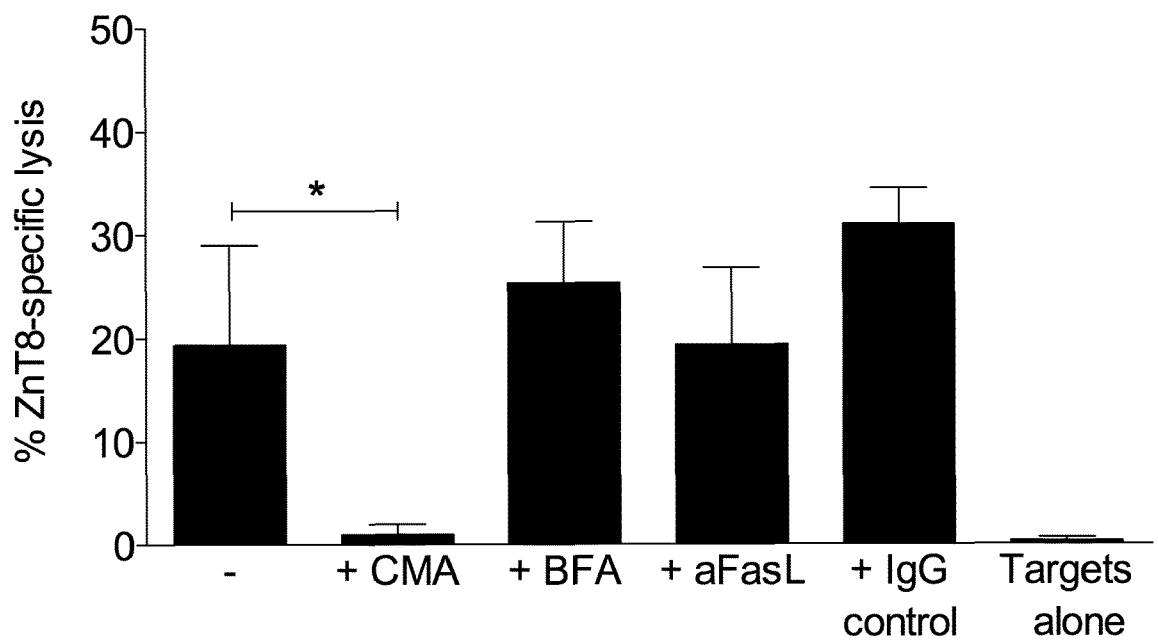

The cytotoxic activity of these $ZnT8_{185-194}$-specific CD8+ T-cell clones was then tested against HLA-A2+ EBV-transformed B-lymphoblastoid LCL cells pulsed with the cognate $ZnT8_{185-194}$ or control peptides (FIG. 6A-B). Increasing numbers of ZnT8-specific T cells led to the complete disappearance of ZnT8—but not control-pulsed targets, with ≥90% lysis obtained for a 1:2 effector/target (E/T) ratio. This lytic activity was dependent on cytotoxic granule release, as it was completely inhibited by concanamycin A, but not by brefeldin A (inhibiting cytokine secretion) or a blocking anti-FasL mAb (inhibiting Fas-dependent cytotoxicity) (FIG. 6C).

Collectively, these results show that ZnT8-specific CD8+ T cells isolated from a T1D patient display strong Ag avidity and cytotoxicity.

$ZnT8_{185-194}$-Specific CD8+ T Cells from Healthy Donors Display Lower Ag Avidity and Polyfunctionality.

Figure 7B:
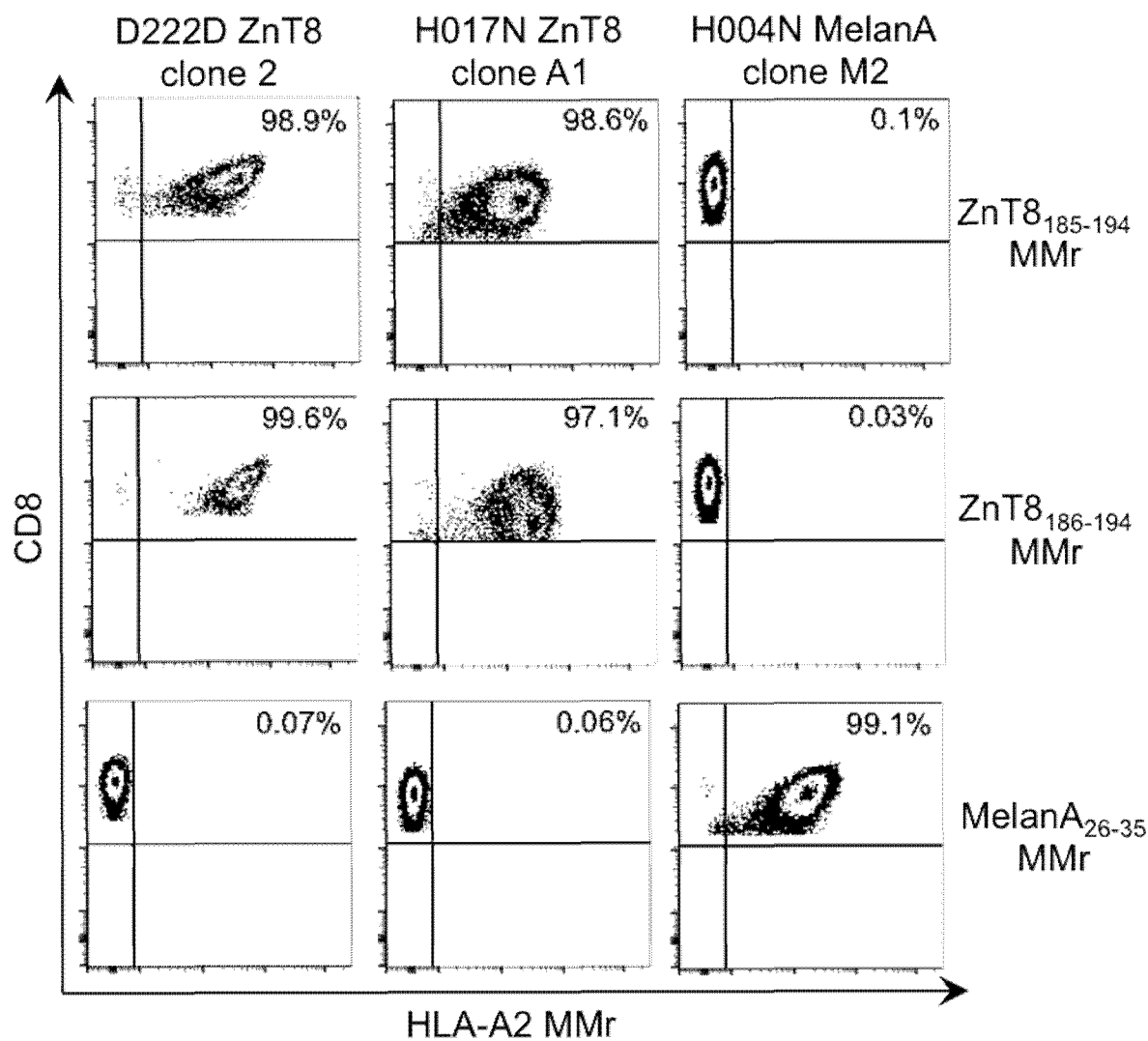
Figure 8A:
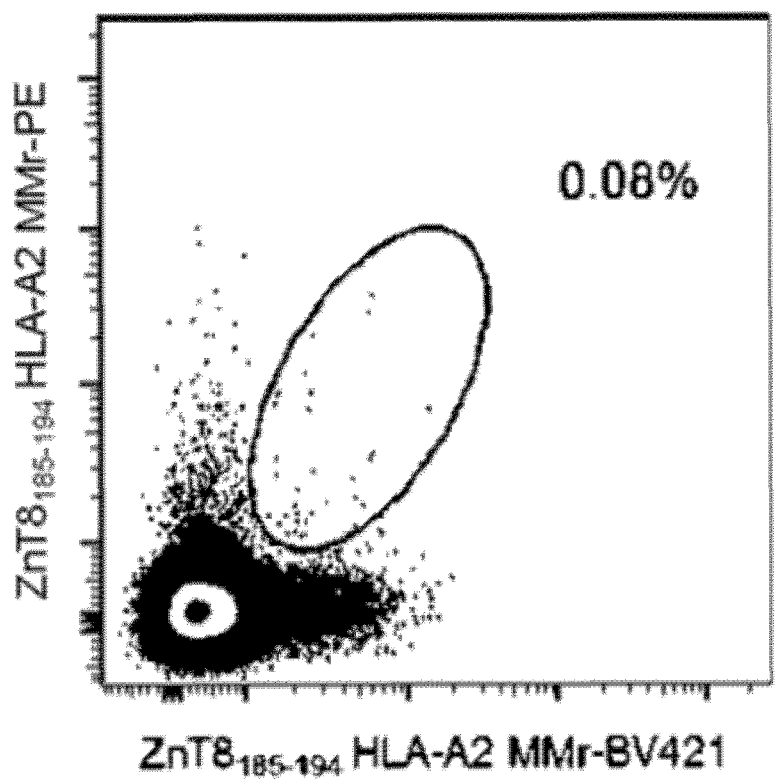
Figure 8B:
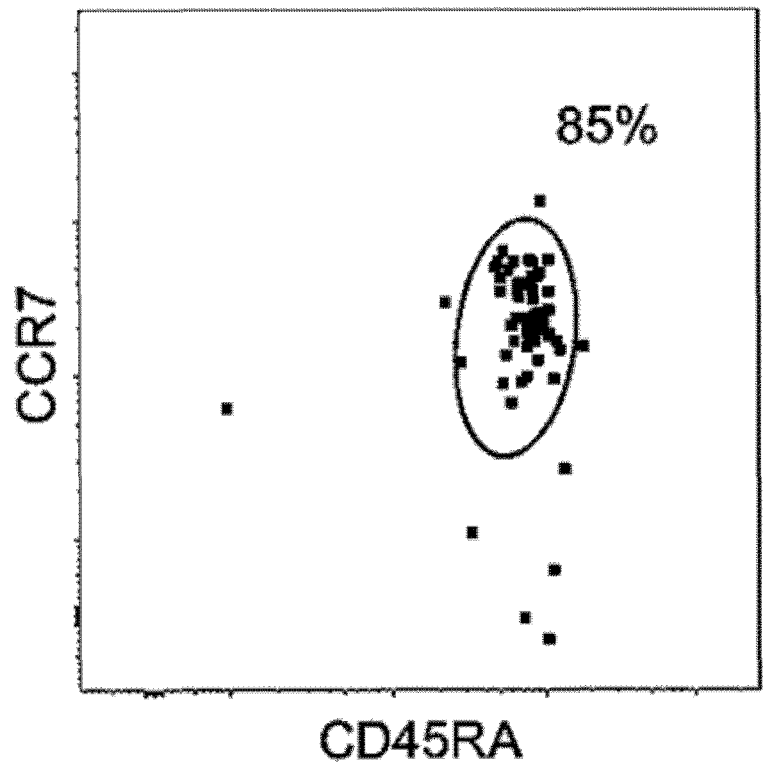
Figure 8C:
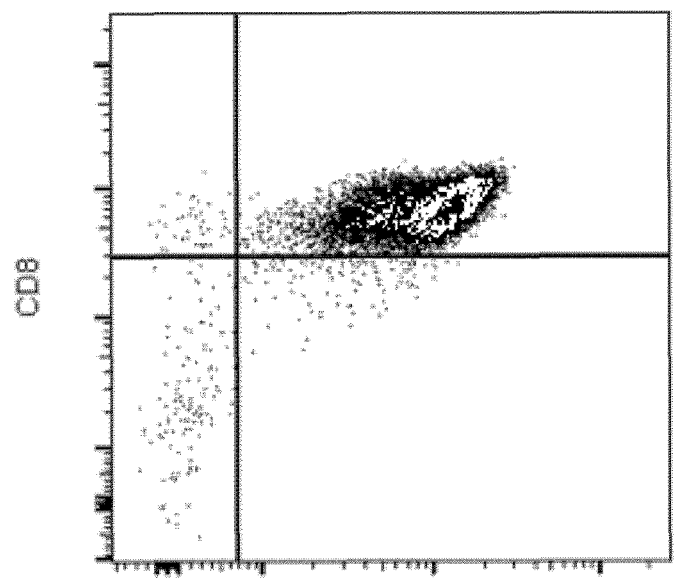
Figure 8D:
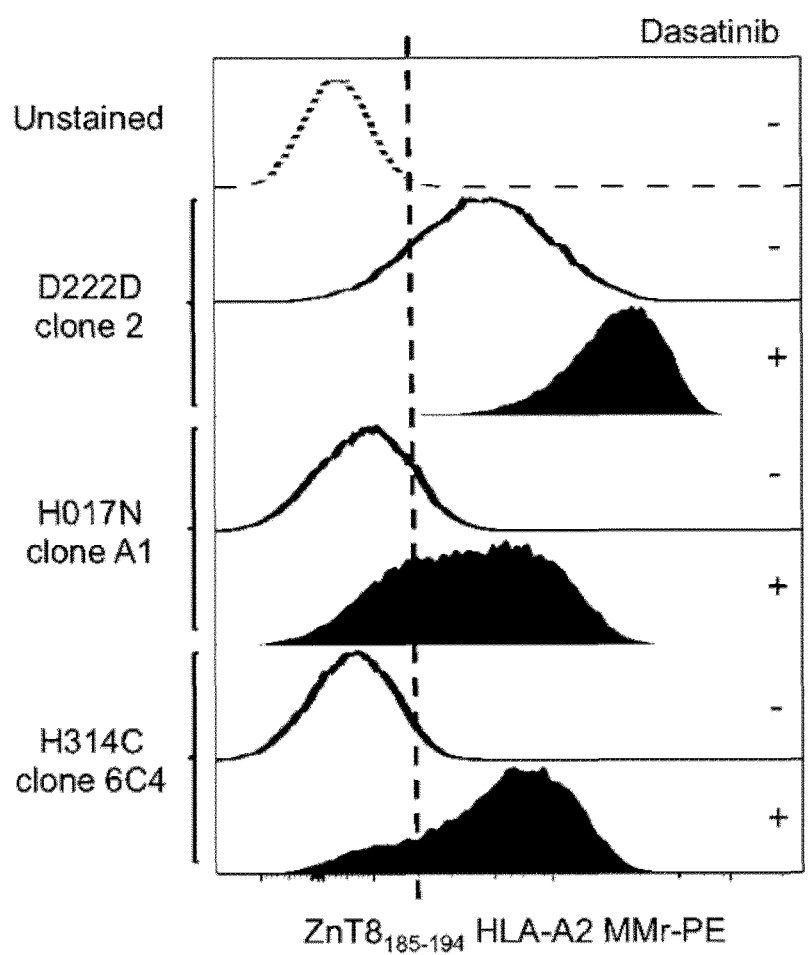
Figure 8E:
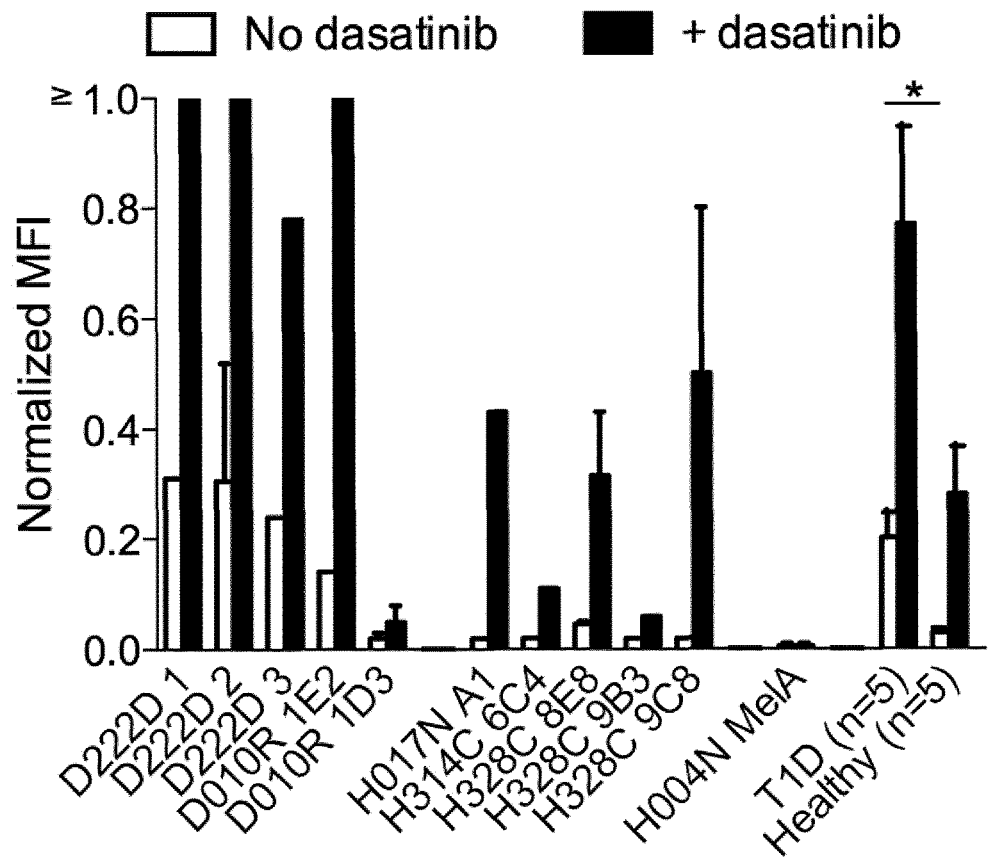

Given the presence of $ZnT8_{185-194}$-specific CD8+ T cells in healthy individuals, these cells were sorted and cloned from three healthy donors (H017N, H314C, H328C) and one additional T1D patient (D010R). Ten clones were thus obtained (FIG. 7A), and all displayed MMr reactivity to both the $ZnT8_{185-194}$ and $ZnT8_{186-194}$ epitope variants (FIG. 7B and data not shown). While healthy clones H017N and H328C were obtained after in vitro acDC expansion as before, the healthy clone H314C 6C4 and T1D clones D010R were sorted directly ex vivo. The parent T cell of clone H314C 6C4 displayed a naïve (CD45RA+CCR7+) phenotype (85% vs. 64% in total CD8+ T cells; FIG. 8A-B-C).

We next aimed at comparing the T-cell avidity of clones obtained from T1D and healthy donors. First, $ZnT8_{185-194}$ MMr staining of these clones displayed higher fluorescence intensity for T1D clones than for healthy ones (FIG. 8D-E), while TCR expression levels were similar in all clones (data not shown). Of note, healthy clones only stained positive in the presence of dasatinib. On the contrary, although dasatinib was able to improve MMr staining, T1D clones stained positive both in the absence and presence of this compound. One exception was noted for the T1D clone D010R 1D3, which displayed weak MMr staining both in the absence and presence of dasatinib (FIG. 8E), possibly reflecting sorting of a minor naïve precursor.

Figure 8F:
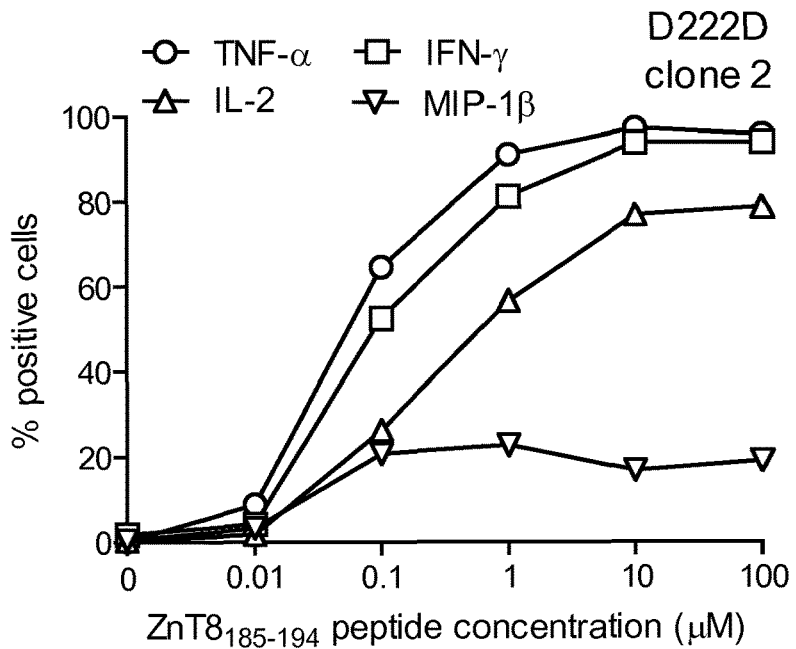
Figure 8G:
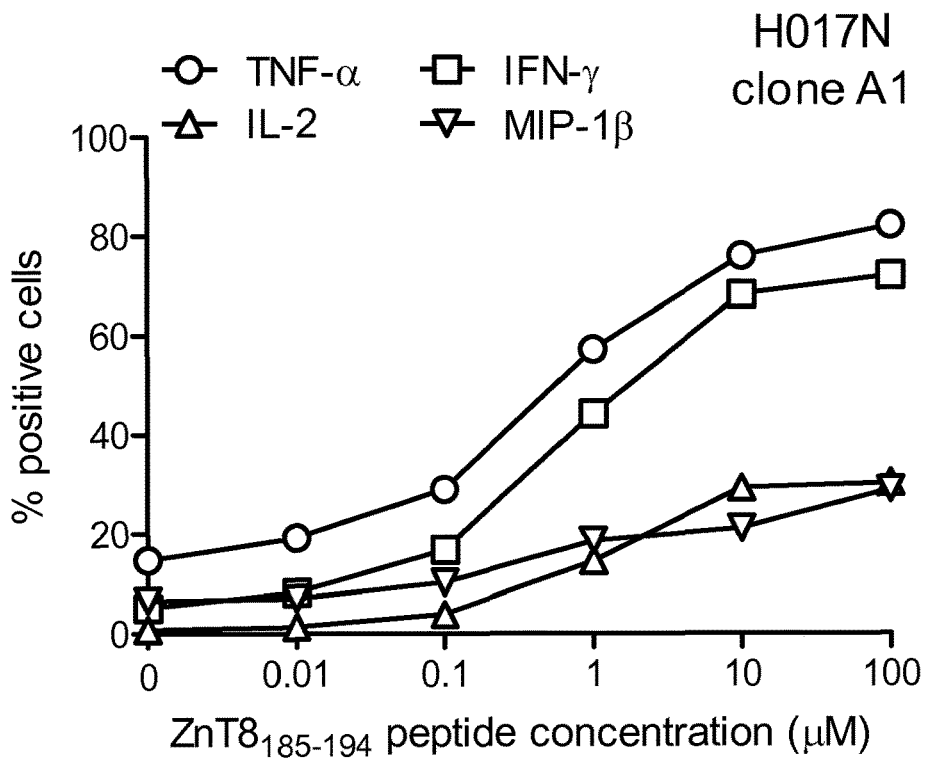
Figure 8H:
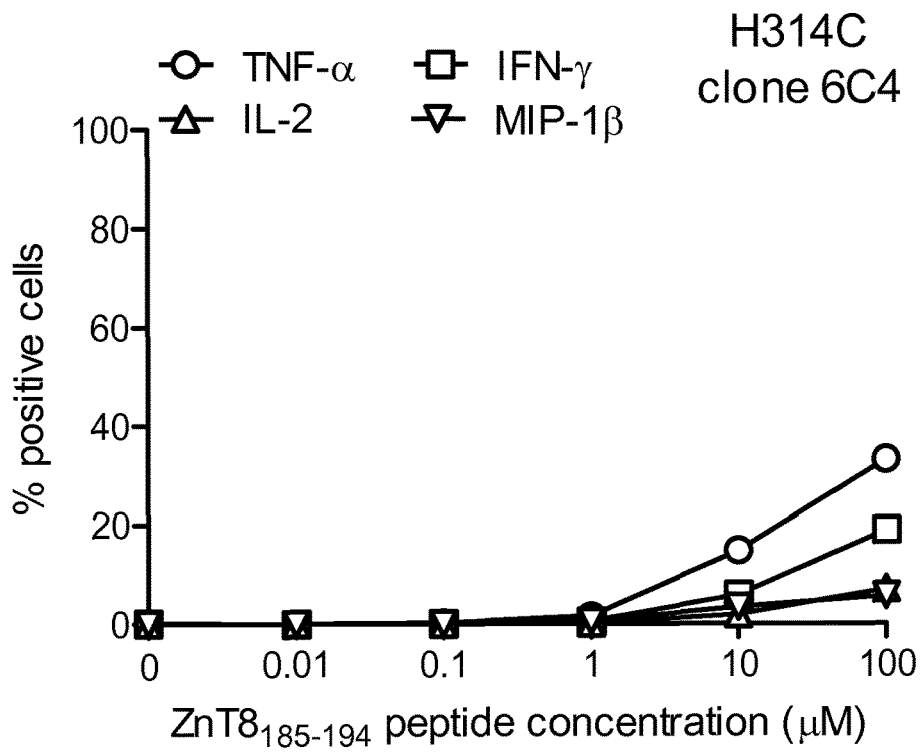
Figure 8I:
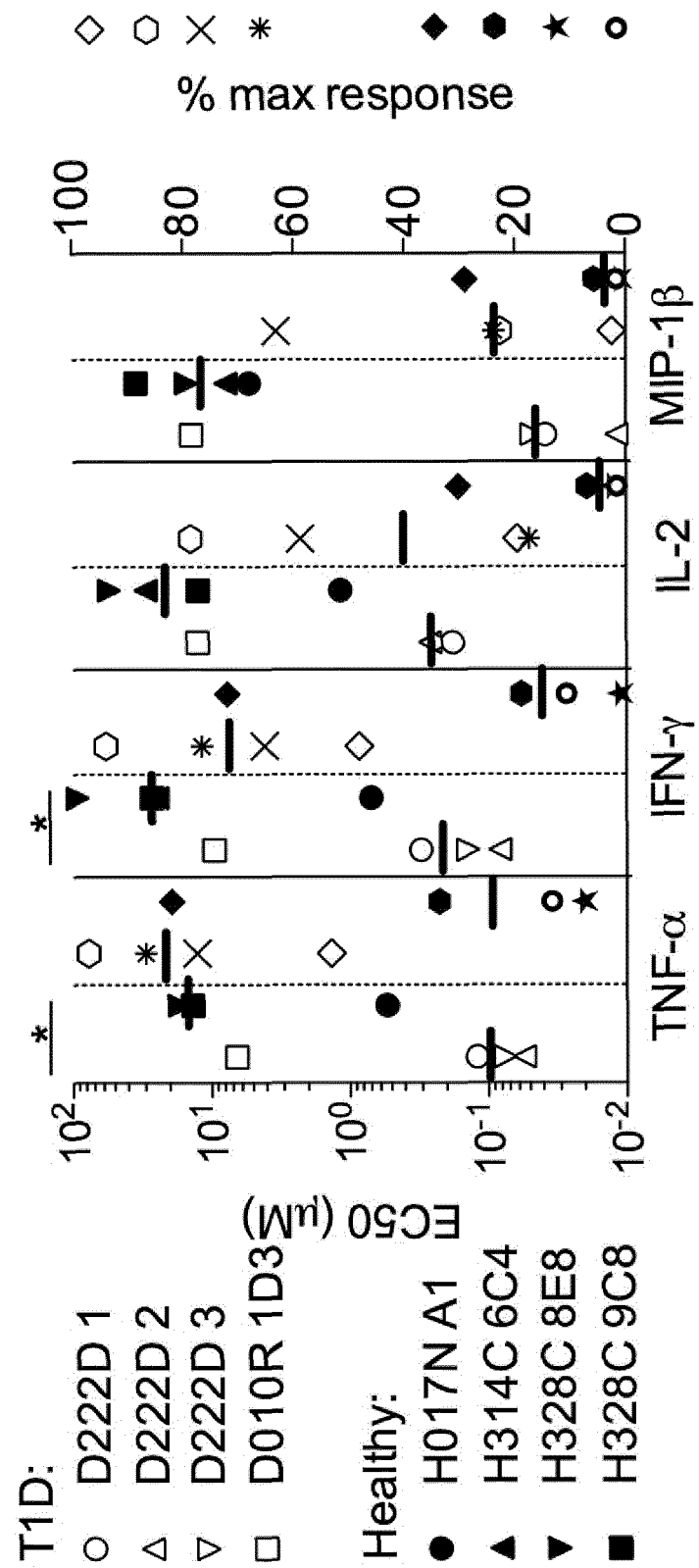
Figure 8J:
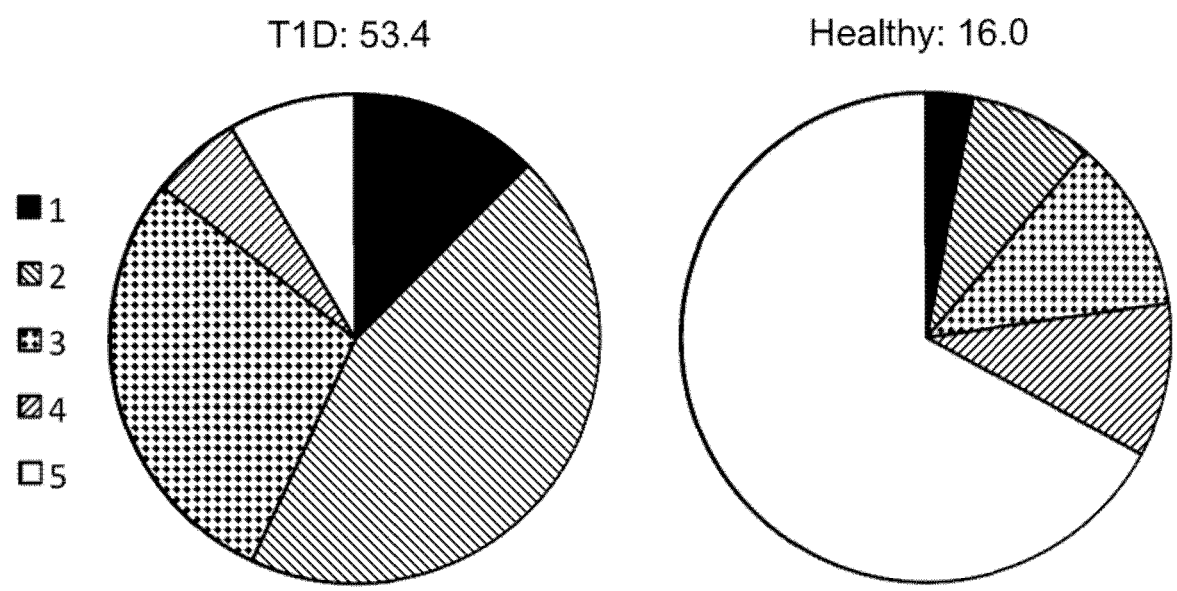

MMr staining intensity usually correlates with the Ag sensitivity of the corresponding T cell (38, 39). To confirm this, in vitro recall assays were performed on these clones in the presence of increasing $ZnT8_{185-194}$ peptide concentrations. Representative assays are shown in FIG. 8F-G-H and results are summarized in FIG. 8I. The half maximal effective peptide concentration (EC50) eliciting TNF-α and IFN-γ responses was significantly lower for T1D clones compared to healthy ones [0.1 (0.06-6.6) vs. 13.7 (0.5-17.2) μM and 0.2 (0.08-9.6) vs. 25.7 (0.7-92.3) μM, respectively; p=0.05), while this difference was not significant for IL-2 and MIP-1β responses. Similar trends were observed for maximal cytokine responses, i.e. when comparing the percent of cytokine-positive T cells at optimal peptide concentrations. Furthermore, the polyfunctionality index, which reflects the number of T cells secreting multiple cytokines and correlates with Ag sensitivity and cytotoxic potency (28), was higher for T1D than for healthy clones (FIG. 8J; 53.4 vs. 16.0; p=0.019).

Collectively, these results show that ZnT8-specific CD8+ T cells isolated from healthy donors display lower Ag avidity and polyfunctionality.

$ZnT8_{185-194}$-Specific CD8+ T Cells from Healthy Donors Display Lower Cytotoxicity.

Figures 9A, 9B:
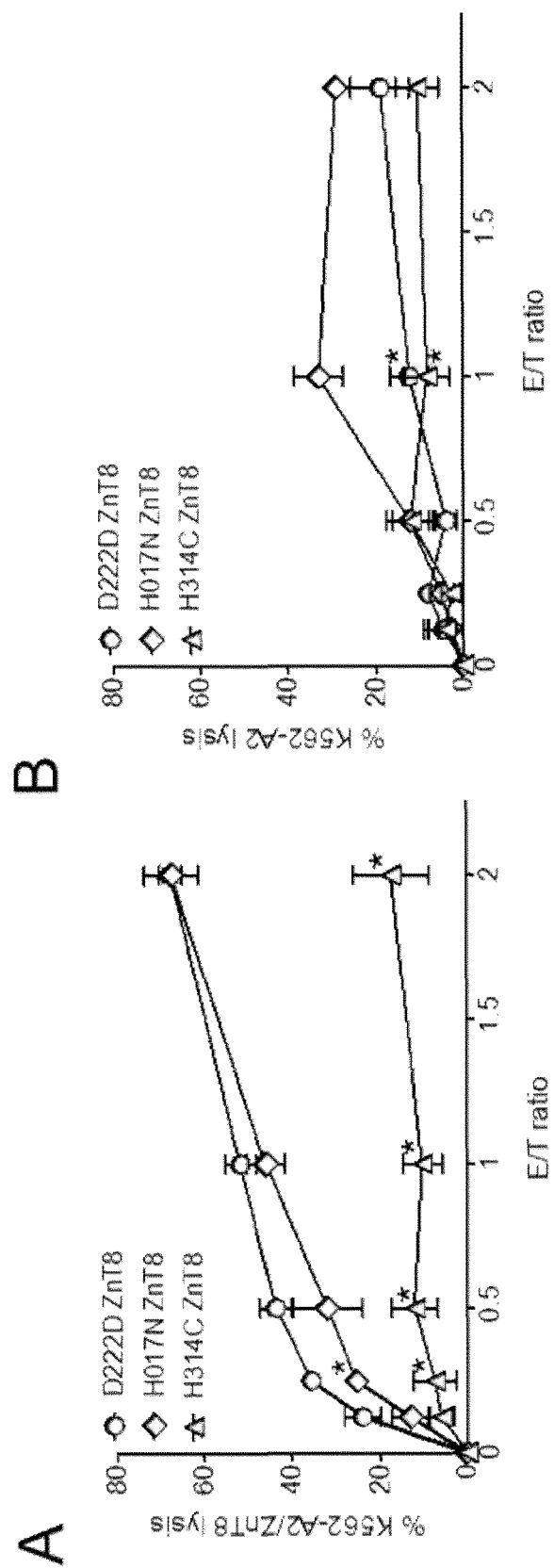
Figure 9C:
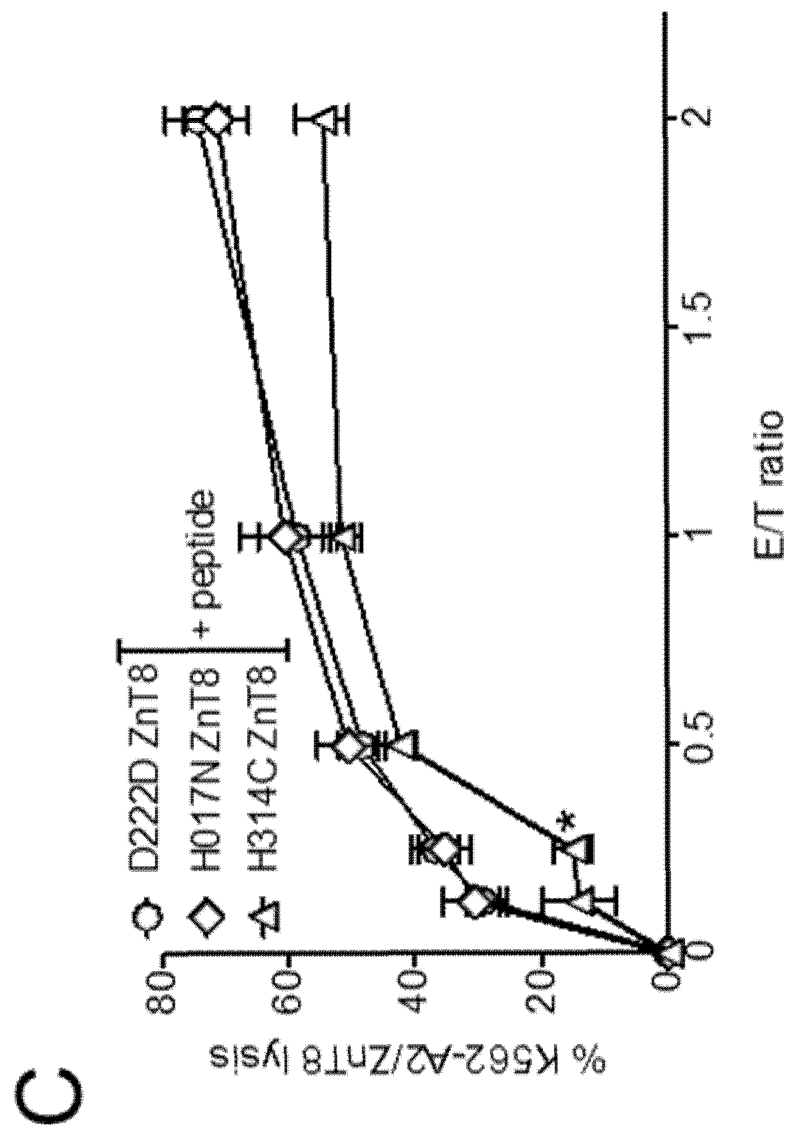
Figures 9D, 9E:
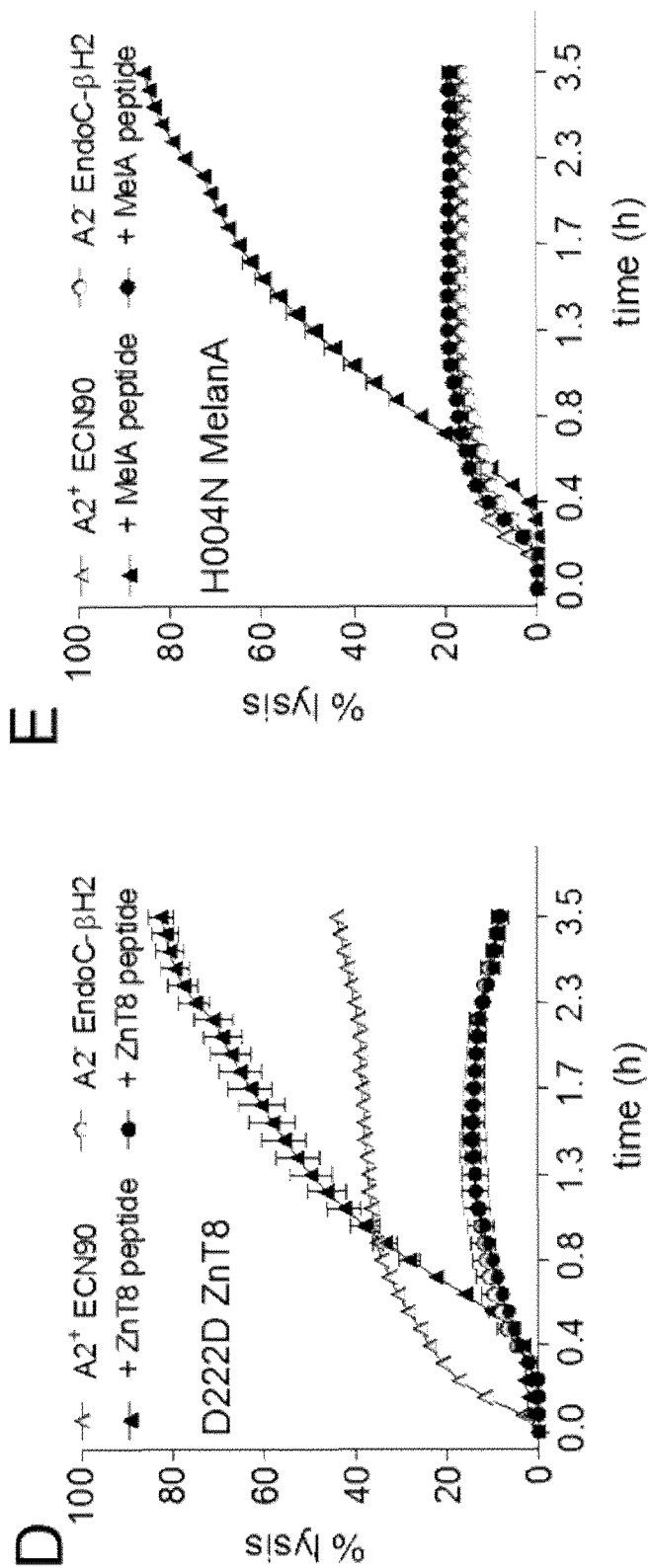

The magnitude of Ag sensitivity usually translates into different cytotoxic potential (3). To test this possibility, we performed cytotoxicity assays using K562-A2 cells that were further transduced with a full-length ZnT8 construct (K562-A2/ZnT8). These target cells also allow us to verify whether $ZnT8_{185-194}$-specific clones are capable of recognizing naturally processed ZnT8 epitopes, which are likely presented at limiting concentrations compared to targets pulsed with exogenous peptide. Indeed, unpulsed K562-A2/ZnT8 targets naturally presenting ZnT8 epitopes were lysed more efficiently by D222D clones as compared to healthy clones, notably at lower E/T ratios (FIG. 9A), despite the fact that the H017N clone displayed higher background cytotoxicity on unpulsed K562-A2 cells not transduced with ZnT8 (FIG. 9B). This difference disappeared once targets were pulsed with excess exogenous $ZnT8_{185-194}$ peptide (FIG. 9C).

Figure 10A:
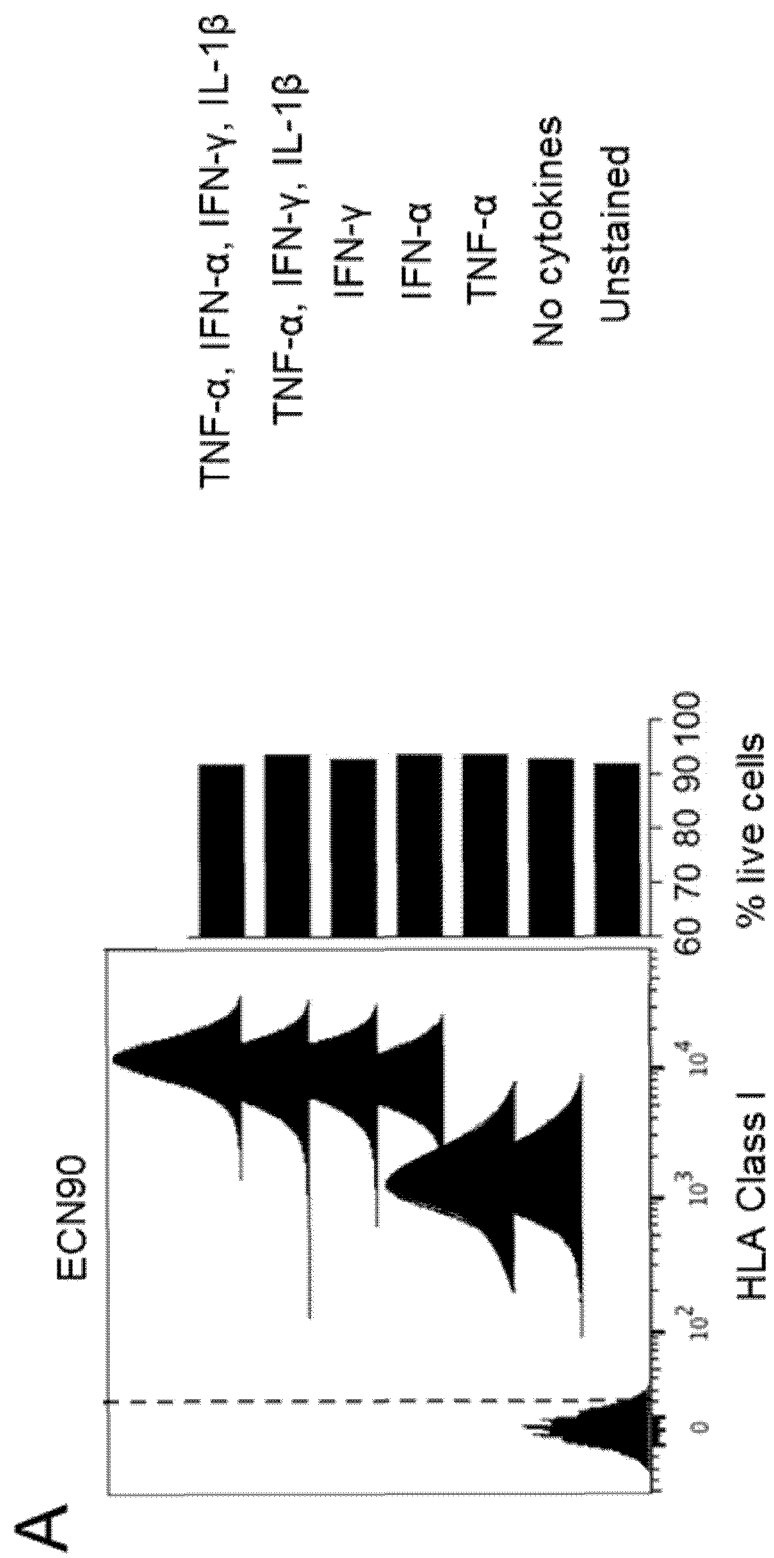
Figure 10B:
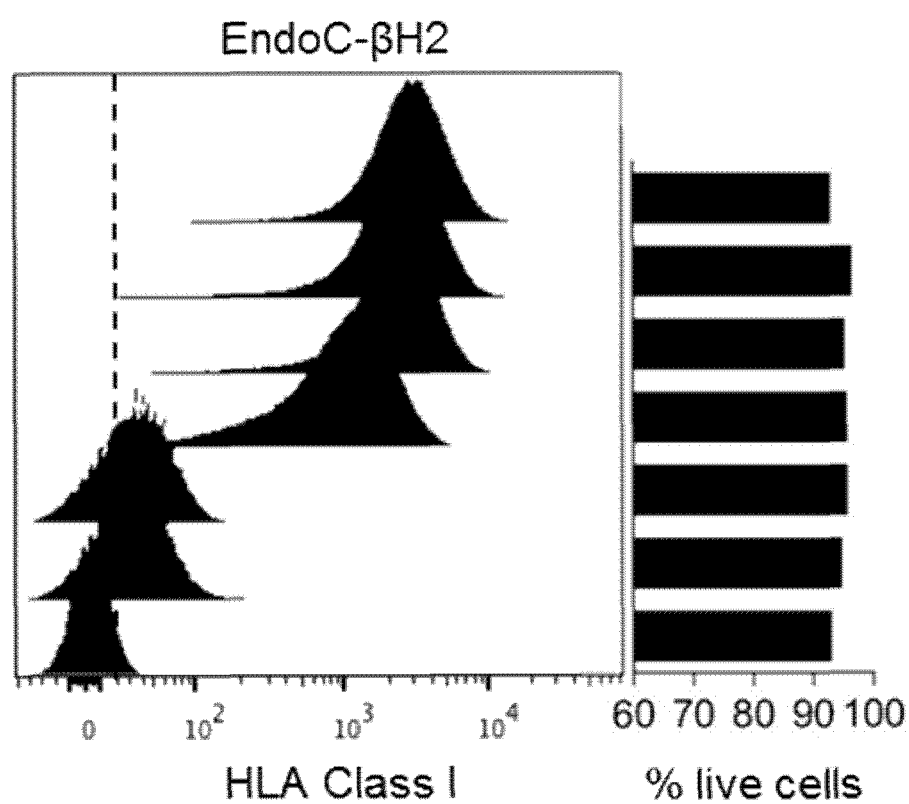
Figures 10C, 10D:
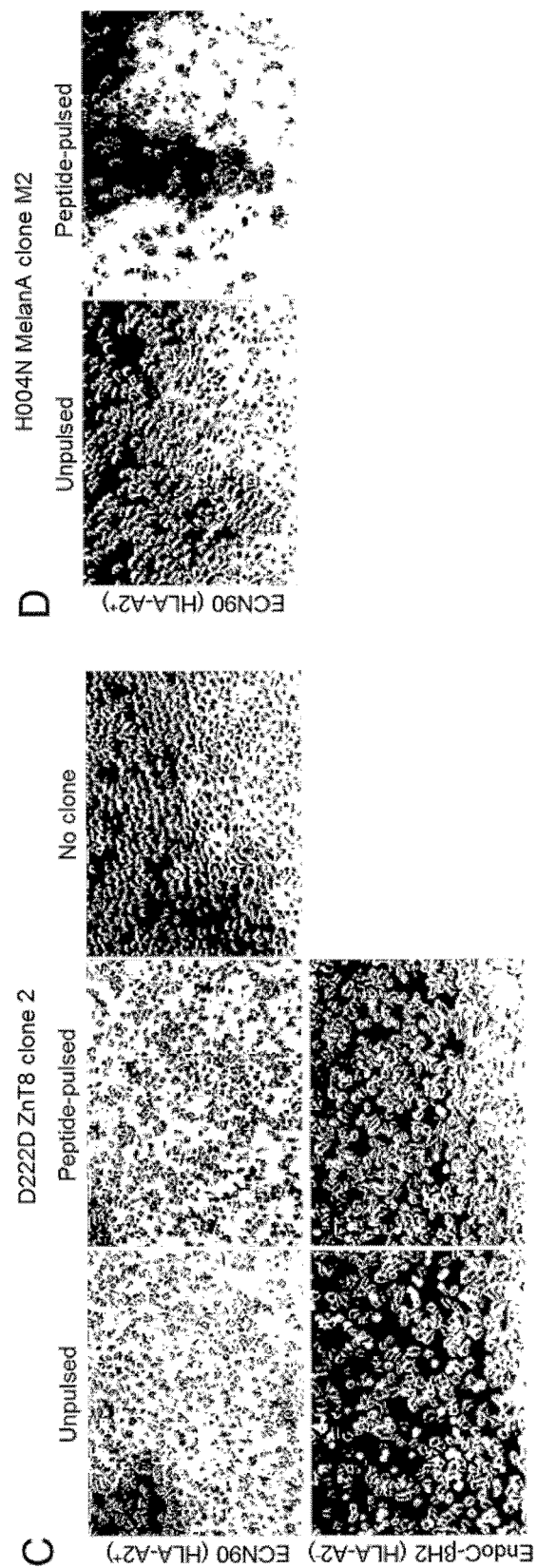

We next wanted to translate these findings into a more T1D-relevant setting, i.e. by using HLA-A2+ ECN90 and control HLA-A2− EndoC-βH2 human β-cell lines. Preliminary experiments showed that, while the ECN90 but not the EndoC-βH2 line expressed HLA Class I in the unstimulated state, this expression could be similarly upregulated by pre-treatment with different cocktails of inflammatory cytokines without inducing significant β-cell death (FIG. 10A-B). IFN-γ was chosen as the single cytokine inducing higher and comparable HLA Class I expression in both lines, and pretreatment was carried out for 18 h before assessing cytotoxicity on a real-time xCELLigence platform. D222D clones were able to lyse unpulsed HLA-A2+ ECN90 cells naturally presenting ZnT8 epitopes (FIG. 9D), and even more upon pulsing with $ZnT8_{185-194}$ peptide. Lysis of HLA-A2− EndoC-βH2 cells (either peptide-pulsed or not) or with a control MelanA$_{26-35}$-specific clone (FIG. 9E) were negligible. Microscopic inspection confirmed that ECN90 but not EndoC-βH2 β cells were effectively killed by D222D T cells (FIG. 10C-D).

Collectively, these results demonstrate that $ZnT8_{185-194}$-specific CD8+ T cells display stronger cytotoxicity in T1D patients compared to healthy donors.

TCR Usage of $ZnT8_{185-194}$-Specific CD8+ T Cells.

TCR sequencing revealed that all three clones obtained from the T1D donor D222D carried the same TCRαβ combination (FIG. 11). This combination was not shared with clones 1E2 and 1D3 derived from T1D patient D010R, although clone 1E2 also displayed usage of TRBV19*01 and TRAJ36*01 genes. Other two TCRs from clones obtained from D027H T1D patient are displayed. Similarly, there were no shared TCR sequences among clones obtained from healthy individuals (FIG. 12), and recurrent TRB and TRA gene usage was also limited, with the exception of TRAV25*01 (shared between clone D010R 1D3 and H328C 9C8) and TRAJ26*01 (shared between clones H314C 6C4 and H328C 9C8). Of further note, the D010R 1E2 TCRβ amino acid sequence was detected in silico in the polyclonal TCR repertoire compiled from CD4$^+$ (both conventional and regulatory) and CD8$^+$ T cells isolated from nPOD pancreatic lymph node and spleen samples. Similar to what observed with cellular assays on PBMCs, positive T1D samples were not more represented than those from control subjects with no known disease or from the few donors available with other pathologies. In particular, a HLA-A2$^+$ subject donor with chronic pancreatitis displayed particularly high D010R TCRβ sequence counts among CD8$^+$ T cells, both in pancreatic lymph nodes and spleen, suggesting that expansion of these cells can occur under conditions of non-autoimmune pancreas inflammation. Nonetheless, all positive hits among CD8$^+$ T cells were confined to pancreatic lymph nodes, and found in the spleen only when present also in the former. Moreover, most of these CD8$^+$ T-cell hits (6/7, 86%) were from pancreatic lymph nodes obtained from HLA-A2$^+$ subjects. The same TCRβ sequence was also detected, to a lesser extent, among conventional and regulatory CD4$^+$ T cells, mostly from pancreatic lymph nodes.

Collectively, these results suggest that $ZnT8_{185-194}$ recognition is mediated primarily by private clonotypes, possibly exhibiting biased TRAV and TRBV gene usage. However, one $ZnT8_{185-194}$-reactive TCRβ CDR3 aminoacid sequence was shared among individuals and found in pancreatic lymph nodes irrespective of disease status.

CONCLUSION

The TCR sequences herein obtained are derived from ZnT8-specific CD8$^+$ T-cell clones generated from T1D and healthy individuals. Some of these clones, particularly those generated from T1D subjects, display very high TCR affinity, which translates into high Ag sensitivity and cytotoxic potential. Thus, the TCR sequences reported in the present invention may be particularly suitable for the proposed applications. TCRs recognizing other β-cell Ags, e.g. PPI and GAD, may display similar characteristics suitable for similar applications.

REFERENCES

Throughout this application, various references describe the state of the art to which this invention pertains. The disclosures of these references are hereby incorporated by reference into the present disclosure.

1. Culina S, Mallone R. Pathogenic and regulatory T cells in type 1 diabetes: losing self-control, restoring it, and how to take the temperature. Curr. Diab. Rep. 2011; 11: 426-33.
2. Skowera A, Ellis R J, Varela-Calvino R et al. CTLs are targeted to kill beta cells in patients with type 1 diabetes through recognition of a glucose-regulated preproinsulin epitope. J. Clin. Invest. 2008; 118: 3390-402.
3. Knight R R, Kronenberg D, Zhao M et al. Human beta-cell killing by autoreactive preproinsulin-specific CD8 T cells is predominantly granule-mediated with the potency dependent upon T-cell receptor avidity. Diabetes 2013; 62: 205-13.
4. Coppieters K T, Dotta F, Amirian N et al. Demonstration of islet-autoreactive CD8 T cells in insulitic lesions from recent onset and long-term type 1 diabetes patients. J. Exp. Med. 2012; 209: 51-60.
5. Mallone R, Roep B O. Biomarkers for immune intervention trials in type 1 diabetes. Clin. Immunol. 2013; 149: 286-96.
6. Fourlanos S, Perry C, Gellert S A et al. Evidence that nasal insulin induces immune tolerance to insulin in adults with autoimmune diabetes. Diabetes 2011; 60: 1237-45.
7. Rosenzwajg M, Churlaud G, Mallone R et al. Low-dose interleukin-2 fosters a dose-dependent regulatory T cell tuned milieu in T1D patients J. Autoimmun. 2015; 58: 48-58.
8. Mallone R, Martinuzzi E, Blancou P et al. CD8+ T-cell responses identify beta-cell autoimmunity in human type 1 diabetes. Diabetes 2007; 56: 613-21.
9. Pittet M J, Zippelius A, Speiser D E et al. Ex vivo IFN-gamma secretion by circulating CD8 T lymphocytes: implications of a novel approach for T cell monitoring in infectious and malignant diseases. J Immunol 2001; 166: 7634-40.
10. Monti P, Scirpoli M, Rigamonti A et al. Evidence for in vivo primed and expanded autoreactive T cells as a specific feature of patients with type 1 diabetes. J. Immunol. 2007; 179: 5785-92.
11. de Jong V M, Abreu J R, Verrijn Stuart A A et al. Alternative splicing and differential expression of the islet autoantigen IGRP between pancreas and thymus contributes to immunogenicity of pancreatic islets but not diabetogenicity in humans. Diabetologia 2013; 56: 2651-8.
12. Skowera A, Ladell K, McLaren J E et al. Beta-cell-specific CD8 T cell phenotype in type 1 diabetes reflects chronic autoantigen exposure. Diabetes 2015; 64: 916-25.
13. Velthuis J H, Unger W W, Abreu J R et al. Simultaneous Detection of Circulating Autoreactive CD8+ T-Cells Specific for Different Islet Cell-Associated Epitopes Using Combinatorial MHC Multimers. Diabetes 2010; 59: 1721-30.
14. Luce S, Lemonnier F, Briand J P et al. Single insulin-specific CD8+ T cells show characteristic gene expression profiles in human type 1 diabetes. Diabetes 2011; 60: 3289-99.
15. Viglietta V, Kent S C, Orban T et al. GAD65-reactive T cells are activated in patients with autoimmune type 1a diabetes. J. Clin. Invest. 2002; 109: 895-903.
16. Arif S, Tree T I, Astill T P et al. Autoreactive T cell responses show proinflammatory polarization in diabetes but a regulatory phenotype in health. J. Clin. Invest. 2004; 113: 451-63.
17. Blancou P, Mallone R, Martinuzzi E et al. Immunization of HLA class I transgenic mice identifies autoantigenic epitopes eliciting dominant responses in type 1 diabetes patients. J Immunol 2007; 178: 7458-66.
18. Scotto M, Afonso G, Larger E et al. Zinc transporter (ZnT)8(186-194) is an immunodominant CD8+ T cell epitope in HLA-A2+ type 1 diabetic patients. Diabetologia 2012; 55: 2026-31.
19. Bonini C, Mondino A. Adoptive T-cell therapy for cancer: the era of engineered T cells. Eur J Immunol 2015.
20. Srivastava S, Riddell S R. Engineering CAR-T cells: Design concepts. Trends Immunol 2015; 36: 494-502.
21. Jensen M C, Riddell S R. Designing chimeric antigen receptors to effectively and safely target tumors. Curr Opin Immunol 2015; 33: 9-15.

22. Gill S, June C H. Going viral: chimeric antigen receptor T-cell therapy for hematological malignancies. Immunol Rev 2015; 263: 68-89.
23. Enee E, Kratzer R, Arnoux J B et al. ZnT8 Is a Major CD8+ T Cell-Recognized Autoantigen in Pediatric Type 1 Diabetes. Diabetes 2012; 61: 1779-84.
24. Hadrup S R, Bakker A H, Shu C J et al. Parallel detection of antigen-specific T-cell responses by multidimensional encoding of MHC multimers. Nat. Methods 2009; 6: 520-26.
25. Andersen R S, Kvistborg P, Frosig T M et al. Parallel detection of antigen-specific T cell responses by combinatorial encoding of MHC multimers. Nature protocols 2012; 7: 891-902.
26. Martinuzzi E, Scotto M, Enee E et al. Serum-free culture medium and IL-7 costimulation increase the sensitivity of ELISpot detection. J. Immunol. Methods 2008; 333: 61-70.
27. Martinuzzi E, Afonso G, Gagnerault M C et al. acDCs enhance human antigen-specific T-cell responses. Blood 2011; 118: 2128-37.
28. Larsen M, Sauce D, Arnaud L et al. Evaluating cellular polyfunctionality with a novel polyfunctionality index. PLoS One 2012; 7: e42403.
29. Eizirik D L, Sandler S, Welsh N et al. Cytokines suppress human islet function irrespective of their effects on nitric oxide generation. J Clin Invest 1994; 93: 1968-74.
30. Leisner C, Loeth N, Lamberth K et al. One-pot, mix-and-read peptide-MHC tetramers. PLoS One 2008; 3: e1678.
31. Lissina A, Ladell K, Skowera A et al. Protein kinase inhibitors substantially improve the physical detection of T-cells with peptide-MHC tetramers. J. Immunol. Methods 2009; 340: 11-24.
32. Ravassard P, Hazhouz Y, Pechberty S et al. A genetically engineered human pancreatic beta cell line exhibiting glucose-inducible insulin secretion. J Clin Invest 2011; 121: 3589-97.
33. Price D A, Brenchley J M, Ruff L E et al. Avidity for antigen shapes clonal dominance in CD8+ T cell populations specific for persistent DNA viruses. J Exp Med 2005; 202: 1349-61.
34. Quigley M F, Almeida J R, Price D A et al. Unbiased molecular analysis of T cell receptor expression using template-switch anchored RT-PCR. Curr Protoc Immunol 2011; Chapter 10: Unit10 33.
35. Lefranc M P, Pommie C, Ruiz M et al. IMGT unique numbering for immunoglobulin and T cell receptor variable domains and Ig superfamily V-like domains.
Developmental and comparative immunology 2003; 27: 55-77.
36. Harndahl M, Rasmussen M, Roder G et al. Peptide-MHC class I stability is a stronger predictor of CTL immunogenicity than peptide affinity. Eur. J. Immunol. 2012; 42: 1405-16.
37. Klein L, Kyewski B, Allen P M et al. Positive and negative selection of the T cell repertoire: what thymocytes see (and don't see). Nat. Rev. Immunol. 2014; 14: 377-91.
38. Mallone R, Kochik S A, Laughlin E M et al. Differential recognition and activation thresholds in human autoreactive GAD-specific T-cells. Diabetes 2004; 53: 971-7.
39. Mallone R, Kochik S A, Reijonen H et al. Functional avidity directs T-cell fate in autoreactive CD4+ T cells. Blood 2005; 106: 2798-805.

The invention claimed is:

1. A zinc transporter 8 (ZnT8)-specific T cell receptor (TCR) comprising an α chain and a β chain, wherein the CDR3 sequences of the β chain and the α chain comprise amino acid sequences as set forth in:
  SEQ ID NO:1 and SEQ ID NO:2 respectively, or
  SEQ ID NO:3 and SEQ ID NO:4 respectively, or
  SEQ ID NO:5 and SEQ ID NO:6 respectively, or
  SEQ ID NO:7 and SEQ ID NO:8 respectively, or
  SEQ ID NO:9 and SEQ ID NO:10 or SEQ ID NO:11 respectively, or
  SEQ ID NO:12 and SEQ ID NO:13 respectively, or
  SEQ ID NO:14 and SEQ ID NO:15 respectively, or
  SEQ ID NO:16 and SEQ ID NO:17 or SEQ ID NO:18 respectively, or
  SEQ ID NO:19 and SEQ ID NO:20 respectively, or
  SEQ ID NO:21 and SEQ ID NO:22 respectively, or
  SEQ ID NO:23 and SEQ ID NO:24 respectively.

* * * * *